(12) United States Patent
Hauling et al.

(10) Patent No.: US 11,352,667 B2
(45) Date of Patent: Jun. 7, 2022

(54) NUCLEIC ACID SEQUENCING

(71) Applicant: 10x Genomics, Inc., Pleasanton, CA (US)

(72) Inventors: Thomas Hauling, Sundbyberg (SE); Malte Kühnemund, Stockholm (SE)

(73) Assignee: 10x Genomics, Inc., Pleasanton, CA (US)

( * ) Notice: Subject to any disclaimer, the term of this patent is extended or adjusted under 35 U.S.C. 154(b) by 466 days.

(21) Appl. No.: 16/312,994

(22) PCT Filed: Jun. 19, 2017

(86) PCT No.: PCT/SE2017/050660
§ 371 (c)(1),
(2) Date: Dec. 21, 2018

(87) PCT Pub. No.: WO2017/222453
PCT Pub. Date: Dec. 28, 2017

(65) Prior Publication Data
US 2019/0161796 A1    May 30, 2019

(30) Foreign Application Priority Data
Jun. 21, 2016 (SE) .................................. 1650869-9

(51) Int. Cl.
*C12Q 1/6874* (2018.01)
*C12Q 1/6876* (2018.01)
*G16B 25/10* (2019.01)
*G16B 25/20* (2019.01)
*C12Q 1/6837* (2018.01)

(52) U.S. Cl.
CPC ......... *C12Q 1/6874* (2013.01); *C12Q 1/6837* (2013.01); *C12Q 1/6876* (2013.01); *G16B 25/10* (2019.02); *G16B 25/20* (2019.02); *C12Q 2600/16* (2013.01)

(58) Field of Classification Search
CPC ............................ C12Q 1/6874; C12Q 1/6876
See application file for complete search history.

(56) References Cited

U.S. PATENT DOCUMENTS

| | | |
|---|---|---|
| 5,695,940 A | 12/1997 | Drmanac et al. |
| 6,238,869 B1 | 5/2001 | Kris |
| 6,306,597 B1 | 10/2001 | Macevicz |
| 6,534,266 B1 | 3/2003 | Singer |
| 7,255,994 B2 | 8/2007 | Lao |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,846,659 B2 | 12/2010 | Cronin et al. |
| 7,910,304 B2 | 3/2011 | Drmanac |
| 7,941,279 B2 | 5/2011 | Hwang et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | Mckernan et al. |
| 8,440,397 B2 | 5/2013 | Drmanac et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,586,312 B2 | 11/2013 | Gentalen et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |

(Continued)

FOREIGN PATENT DOCUMENTS

WO    02/057491 A2    7/2002
WO    02/101358 A2    12/2002

(Continued)

OTHER PUBLICATIONS

Ke, R. et al., In situ sequencing for RNA analysis in preserved tissue and cells, Nature Methods, vol. 10, supplemental material, pp. 1-29 (Year: 2013).*
Extended European Search Report dated Jan. 8, 2020, issued in corresponding EP Application No. 17815813.5, 6 pages.
4 Month Notice and Search Report of corresponding SE Application No. 1650869-9, dated Jan. 20, 2017, 9 pages.
Ke et al., "In situ sequencing for RNA analysis in preserved tissue and cells", Nature Methods, Sep. 2013, pp. 857-862, vol. 10 No. 9.
Shendure et al., "Accurate Multiplex Polony Sequencing of an Evolved Bacterial Genome", Science, Sep. 9, 2005, pp. 1728-1732, vol. 309.
Pacureanu et al.,"Image Based In Situ Sequencing for RNA Analysis in Tissue", IEEE 11th International Symposium on Biomedical Imaging, 2014, pp. 286-289.

(Continued)

*Primary Examiner* — Teresa E Strzelecka
(74) *Attorney, Agent, or Firm* — Morrison & Foerster LLP

(57) ABSTRACT

A nucleic acid sequencing method involving contacting a spatially defined target nucleic acid sequence with N labeled oligonucleotide probes and performing measurements, at least at the spatially defined site (1), at M time instances during ligation or hybridization to form M data sets. The M data sets are co-processed in order to identify a label or absence of any label at the spatially defined site (1). A sequenced based of the target nucleic acid sequence is then determined based on the identified label of the identified absence of any label. The time-resolved measurements conducted during the actual hybridization of the oligonucleotide probes to the target nucleic acid sequence or the ligation of oligonucleotide probes to anchor probes on the target nucleic acid sequence improves the speed and accuracy of the sequencing as compared to the state of the art sequencing methods.

20 Claims, 20 Drawing Sheets

Specification includes a Sequence Listing.

(56) References Cited

U.S. PATENT DOCUMENTS

| | | |
|---|---|---|
| 9,376,717 B2 | 6/2016 | Gao et al. |
| 9,541,504 B2 | 1/2017 | Hoyt |
| 9,624,538 B2 | 4/2017 | Church et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 2006/0229824 A1 | 10/2006 | Cronin et al. |
| 2007/0264641 A1 | 11/2007 | Li et al. |
| 2008/0269068 A1 | 10/2008 | Church et al. |
| 2011/0039304 A1 | 2/2011 | Church et al. |
| 2012/0129165 A1 | 5/2012 | Raj et al. |
| 2014/0024542 A1 | 1/2014 | Richards et al. |
| 2015/0368704 A1 | 12/2015 | Fan et al. |
| 2016/0108458 A1 | 4/2016 | Frei et al. |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0029872 A1 | 2/2017 | Bhattacharyya et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0332368 A1 | 10/2020 | Ferree et al. |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-darling et al. |
| 2021/0017587 A1 | 1/2021 | Cai et al. |
| 2021/0115504 A1 | 4/2021 | Cai et al. |

FOREIGN PATENT DOCUMENTS

| | | |
|---|---|---|
| WO | WO02074988 A3 | 8/2003 |
| WO | 2004/007755 A2 | 1/2004 |
| WO | 2007/106509 A2 | 9/2007 |
| WO | 2007/133831 A2 | 11/2007 |
| WO | 2008/070352 A2 | 6/2008 |
| WO | 2008/127901 A1 | 10/2008 |
| WO | 2008/134867 A1 | 11/2008 |
| WO | 2012/149171 A1 | 11/2012 |
| WO | 2013/109731 A1 | 7/2013 |
| WO | 2014/030066 A2 | 2/2014 |
| WO | 2014/182528 A2 | 11/2014 |
| WO | 2015/031691 A1 | 3/2015 |
| WO | 2015/047186 A1 | 4/2015 |
| WO | 2016/007063 A1 | 1/2016 |
| WO | 2016/007839 A1 | 1/2016 |
| WO | 2016/138496 A1 | 9/2016 |
| WO | 2016/138500 A1 | 9/2016 |
| WO | 2016/149418 A1 | 9/2016 |
| WO | 2016/160844 A2 | 10/2016 |
| WO | 2016/172373 A1 | 10/2016 |
| WO | 2017143155 A2 | 8/2017 |
| WO | 2019199579 A1 | 10/2019 |
| WO | 2020076976 A1 | 4/2020 |
| WO | 2020076979 A1 | 4/2020 |
| WO | 2020096687 A1 | 5/2020 |
| WO | 2020099640 A1 | 5/2020 |
| WO | 2020117914 A1 | 6/2020 |
| WO | 2020123742 A1 | 6/2020 |
| WO | 2020142490 A1 | 7/2020 |
| WO | 2020240025 A1 | 12/2020 |
| WO | 2020254519 A1 | 12/2020 |

OTHER PUBLICATIONS

Lee et al., "Highly multiplexed subcellular RNA sequencing in Situ", Science, Mar. 21, 2014, pp. 1360-1363, vol. 343 (6177).

Peng, "Sequential Color Display for Highly Multiplexed In Situ Single-Molecular Detection", A Dissertation Submitted to the Department of Applied Physics and the Committee on Graduate Studies of Stanford University in Partial Fulfillment of the Requirement for the Degree of Doctor of Philosophy, Jun. 2017, 114 pages.

Kamentsky et al., "Improved structure, function and compatibility for CellProfiler: Modular high-throughput image analysis software", Bioinformatics Advance Access published Feb. 23, 2011, 3 pages.

Jungmann et al., "Multiplexed 3D cellular super-resolution imaging with DNA-PAINT and Exchange-PAINT", Nature Methods, Mar. 2014, pp. 313-321, vol. 11 No. 3.

Goh, J.J.L. et al. (Jul. 2020, e-pub. Jun. 15, 2020). "Highly Specific Multiplexed RNA Imaging in Tissues With Split-FISH," Nat Methods 17(7):689-693.

Goransson, J. et al. (Jan. 2009, e-pub. Nov. 25, 2008). "A Single Molecule Array for Digital Targeted Molecular Analyses," Nucleic Acids Res 37(1):e7, 9 pages.

(56) References Cited

OTHER PUBLICATIONS

Liu, S. et al. (2021, e-pub. Mar. 8, 2021). "Barcoded Oligonucleotides Ligated on RNA Amplified for Multiplexed and Parallel In Situ Analyses," Nucleic Acids Res. 49(10):e58, 15 pages.
Payne, A.C. et al. (Feb. 26, 2021, e-pub Dec. 31, 2020). "In Situ Genome Sequencing Resolves DNA Sequence and Structure in Intact Biological Samples," Science 371(6532):1-19, 20 pages.
Rouhanifard, S.H. et al. (Nov. 12, 2018, e-pub. May 13, 2019). "Clampfish Detects Individual Nucleic Acid Molecules Using Click Chemistry-Based Amplification," Nat Biotechnol, 17 pages.
Takei, Y. et al. (Feb. 2021, e-pub Jan. 27, 2021). "Integrated Spatial Genomics Reveals Global Architecture of Single Nuclei," Nature 590(7845):344-350, 53 pages.
Wu, C. et al. (Nov. 28, 2018). "RollFISh Achieves Robust Quantification of Single-Molecule RNA Biomarkers in Paraffin-Embedded Tumor Samples," Commun Biol. 1:(209):1-8.

\* cited by examiner

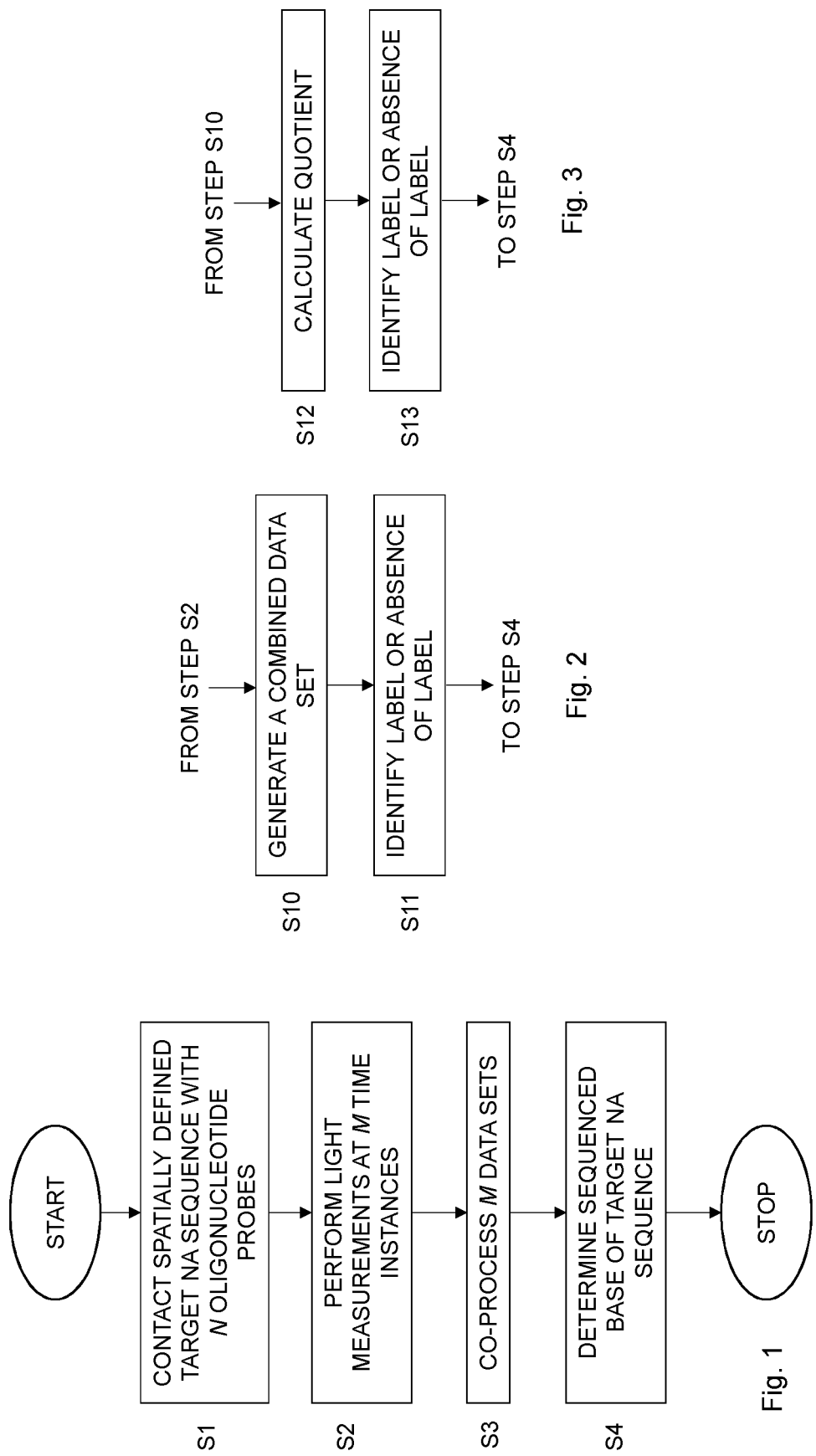

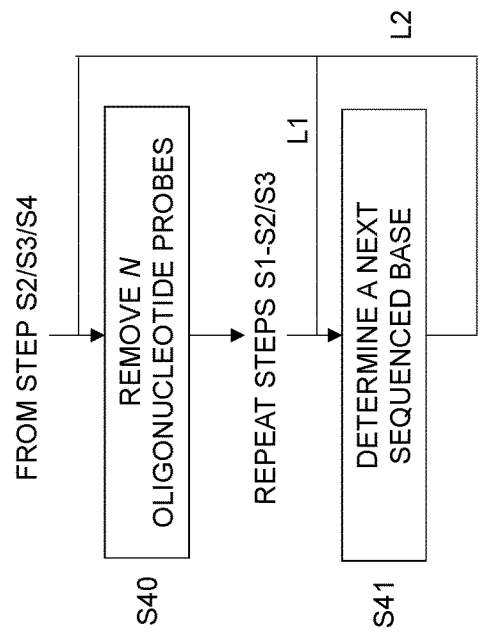
Fig. 6
Fig. 5
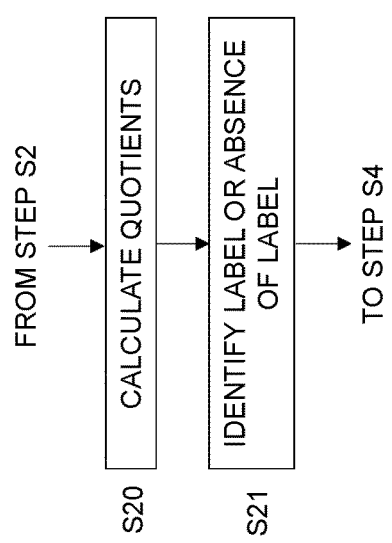
Fig. 4

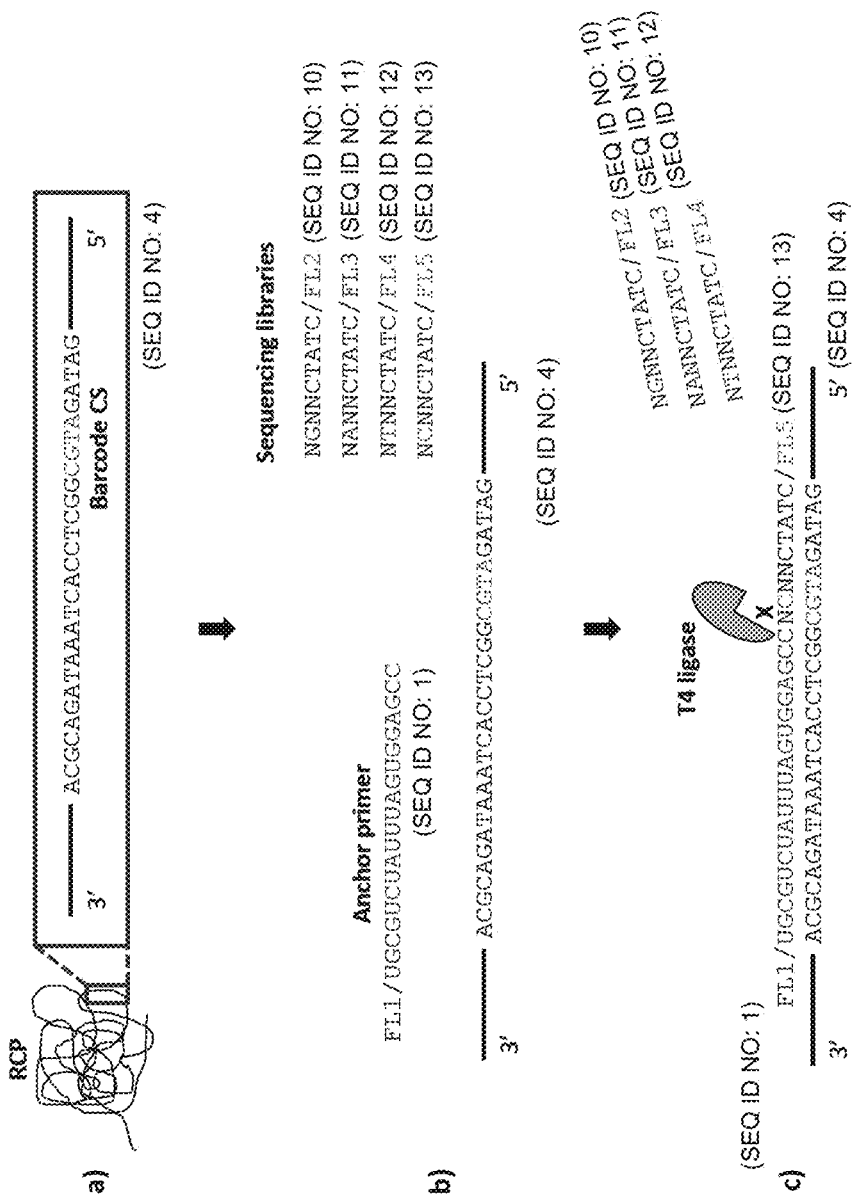
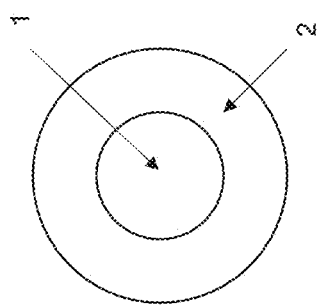
Fig. 7
Fig. 8

Seq oligos

1st base
TNNN CTATC - AF488 (Alexa Fluor 488) (dye)
GNNN CTATC - Cy3 (dye)
CNNN CTATC - Texred (dye)
ANNN CTATC - Cy5 (dye)

2nd base
NTNN CTATC - AF488 (Alexa Fluor® 488) (dye)
NGNN CTATC - Cy®3 (dye)
NCNN CTATC - Texas Red® (dye)
NANN CTATC - Cy®5 (dye)

3rd base
NNTN CTATC - AF488 (Alexa Fluor® 488) (dye)
NNGN CTATC - Cy®3 (dye)
NNCN CTATC - Texas Red® (dye)
NNAN CTATC - Cy®5 (dye)

Fig. 16B

Fig. 17A   Sequencing oligos   (SEQ ID NO: 19) (dye)   (SEQ ID NO: 20)
           1st base              CNNNNNNNN-Texas Red®   TNNNNNNNN - FitC
                                 ANNNNNNNN - Cy®5 (dye)  GNNNNNNNN - Cy®3 (dye)
                                 (SEQ ID NO: 20)         (SEQ ID NO: 21)

Fig. 17B   Anchor oligo          GNNNNNNNN - Cy®3 (dye) (SEQ ID NO: 21)
           common                unknown sequence
           anchor sequence Fig. 17C   (Alexa Fluor® 750)
           (dye)AF750 - TGCGTCTATTTAGTGGAGCCGNNNNNNNN - Cy®3 (dye) (SEQ ID NO: 23)
           ...CACTAAATGAXCGCAGTCAGTAATC... AAGAAGATAGATAXGCCTCACTAAATGAXCGCAGTCAGTAAXAA (SEQ ID NO: 24)

NUCLEIC ACID SEQUENCING

CROSS-REFERENCE TO RELATED APPLICATIONS

The present application is a U.S. National Phase patent application and claims priority to and the benefit of International Application Number PCT/SE2017/050660, filed on Jun. 19, 2017, which claims priority to and the benefit of Swedish Patent Application Number 1650869-9, filed on Jun. 21, 2016, the entire contents of all of which are incorporated herein by reference.

INCORPORATION BY REFERENCE

The instant application contains a Sequence Listing which has been submitted in ASCII format via EFS-Web and is hereby incorporated by reference in its entirety. Said ASCII copy was modified on Aug. 25, 2021, is named 202412008300SubSeqList.txt, and is 9,339 bytes in size.

TECHNICAL FIELD

The present embodiments generally relate to nucleic acid sequencing, and in particular to such nucleic acid sequencing performed based on time-resolved measurements.

BACKGROUND

Fluorescence-based next generation sequencing methods rely on the incorporation, hybridization or ligation of fluorescently labeled single nucleotides or short fluorescently labeled oligonucleotides to a target nucleic acid sequence in a nucleic acid molecule. Nucleic acid sequences can, for instance, be determined through sequencing by ligation (SBL) or sequencing by hybridization (SBH). In SBL, short fluorescently labeled oligonucleotides complementary to a portion of the target nucleic acid sequence are ligated to adjacent anchor primers hybridized to the nucleic acid molecule. In SBH, short fluorescently labeled oligonucleotides are hybridized to a complementary sequence in the target nucleic acid sequence. Alternatively, the target nucleic acid sequence itself is fluorescently labeled and hybridized to an array.

In SBL and SBH, typically one base at a time is sequenced. A sequencing reaction of one base typically consists of a plurality of steps: (i) application and incubation of reaction mixture including fluorescently labeled oligonucleotides, (ii) removal of reaction mixture, (iii) washing, and (iv) an end-point fluorescent measurement. The purpose of removing the reaction mixture and washing is to remove unreacted fluorescently labeled oligonucleotides, after which predominantly the correct complementary oligonucleotide remains. This removal and washing thereby reduces the background or noise and increases the signal-to-noise ratio (SNR).

In most SBL and SBH applications, long reaction and reaction incubation times, such as 30-60 min, are required in order to achieve sufficient incorporation of the correct fluorescently labeled oligonucleotide. This is necessary to distinguish the correct base-specific staining from unspecific background when performing an end-point measurement. The length of the incubation and reaction time together with the removal and washing steps are the main speed and throughput limitations for the current sequencing technologies.

Furthermore, the accuracy of sequencing reactions using end-point measurements is limited by false-read errors that can occur due to misinterpretation of auto-fluorescence and clusters of fluorescently labeled oligonucleotides as sequence-specific signals, or due to unspecific incorporation of fluorescently labeled oligonucleotides.

Examples of such prior art sequencing relying on end-point measurements are presented in [3, 4]. Document [3] discloses in situ sequencing of single RNA molecules directly in the tissue environment. Document [4] discloses a multiplex polony sequencing of *Escherichia coli* genome.

Hence, there is a need for improvement within the field of nucleic acid sequencing.

SUMMARY

It is a general objective to provide an efficient nucleic acid sequencing.

It is a particular objective to provide a nucleic acid sequencing that is fast and accurate.

These and other objectives are met by embodiments as disclosed herein.

The present invention relates to a nucleic acid sequence method as defined in the independent claim. Further embodiments are defined in the dependent claims.

The nucleic acid sequencing method comprises contacting a spatially defined, at a spatially defined site, target nucleic acid sequence with $N≥1$ oligonucleotide probes. If $N=1$, the oligonucleotide probe has a label, and if $N≥2$, each oligonucleotide probe of the N oligonucleotide probes has a nucleic acid sequence that is different from nucleic acid sequences of the other $N-1$ oligonucleotide probes of the N oligonucleotide probes. If $N≥2$, the N oligonucleotide probes have different labels or an oligonucleotide probe of the N oligonucleotide probes lacks a label and the other $N-1$ oligonucleotide probes of the N oligonucleotide probes have different labels. The method also comprises performing measurements, at least at the spatially defined site, at $M≥2$ time instances during i) a hybridization reaction comprising hybridization of the N oligonucleotide probes to the target nucleic acid sequence or ii) a ligation reaction comprising ligation of the N oligonucleotide probes to an anchor probe complementary to a segment of a nucleic acid molecule comprising the target nucleic acid sequence to form M data sets. The method further comprises co-processing the M data sets in order to identify a label or absence of any label at the spatially defined site. The method additionally comprises determining a sequenced base of the target nucleic acid sequence based on the identified label or the identified absence of any label.

The present nucleic acid sequencing is based on time-resolved measurements and is significantly faster than the prior art sequencing methods since the measurements are performed during the actual incorporation, hybridization or ligation reaction. Accordingly, it is not necessary to await the end of any incubation and reaction period. The present embodiments may also improve the accuracy of nucleic acid sequencing. The reason being that the prior art sequencing methods, based on end-point measurements, are limited by false read errors that can occur due to misinterpretation of, for instance, auto fluorescence and clusters of fluorescently labeled oligonucleotides as sequence specific signals, or due to unspecific incorporation of fluorescently labeled oligonucleotides. The co-processing of multiple measurements performed during the reaction according to the present embodiments reduces the risk of such false read errors.

BRIEF DESCRIPTION OF THE DRAWINGS

The embodiments, together with further objects and advantages thereof, may best be understood by making reference to the following description taken together with the accompanying drawings, in which:

FIG. 1 is a flow chart illustrating a nucleic acid sequencing method according to an embodiment.

FIG. 2 is flow chart illustrating an embodiment of the co-processing step in FIG. 1.

FIG. 3 is a flow chart illustrating an embodiment of the identifying step in FIG. 2.

FIG. 4 is a flow chart illustrating another embodiment of the co-processing step in FIG. 1.

FIG. 5 is a flow chart illustrating an additional, optional step of the nucleic acid sequencing method in FIG. 1.

FIG. 6 is a flow chart illustrating additional, optional steps of the nucleic acid sequencing method in FIG. 1.

FIG. 7 schematically shows a spatially defined site or area (inner circle) and its local background exemplified as a donut-shaped area surrounding the inner area.

FIG. 8 schematically illustrates sequencing by ligation (SBL) of a nucleic acid accumulation (NAA) generated by rolling circle amplification (RCA) to form a RCA product (RCP). One sequencing cycle is depicted. The interrogation of guanine (G) at base position 2 of a CGTA barcode complementary sequence (barcode CS) is shown. a) RCPs contain multiple copies of the barcode CS. b) A fluorophore-labeled (FL1) anchor primer and fluorophore-labeled (FL2-FL5) 9-mer oligonucleotide probes that interrogate position 2 of the barcode CS are added. c) The anchor primer hybridizes to the complementary sequence in the RCP, upstream of the barcode CS. Individual oligonucleotide probes of the sequencing libraries interrogate the barcode CS. Perfectly matching probes are ligated.

DETAILED DESCRIPTION

Figure 9:
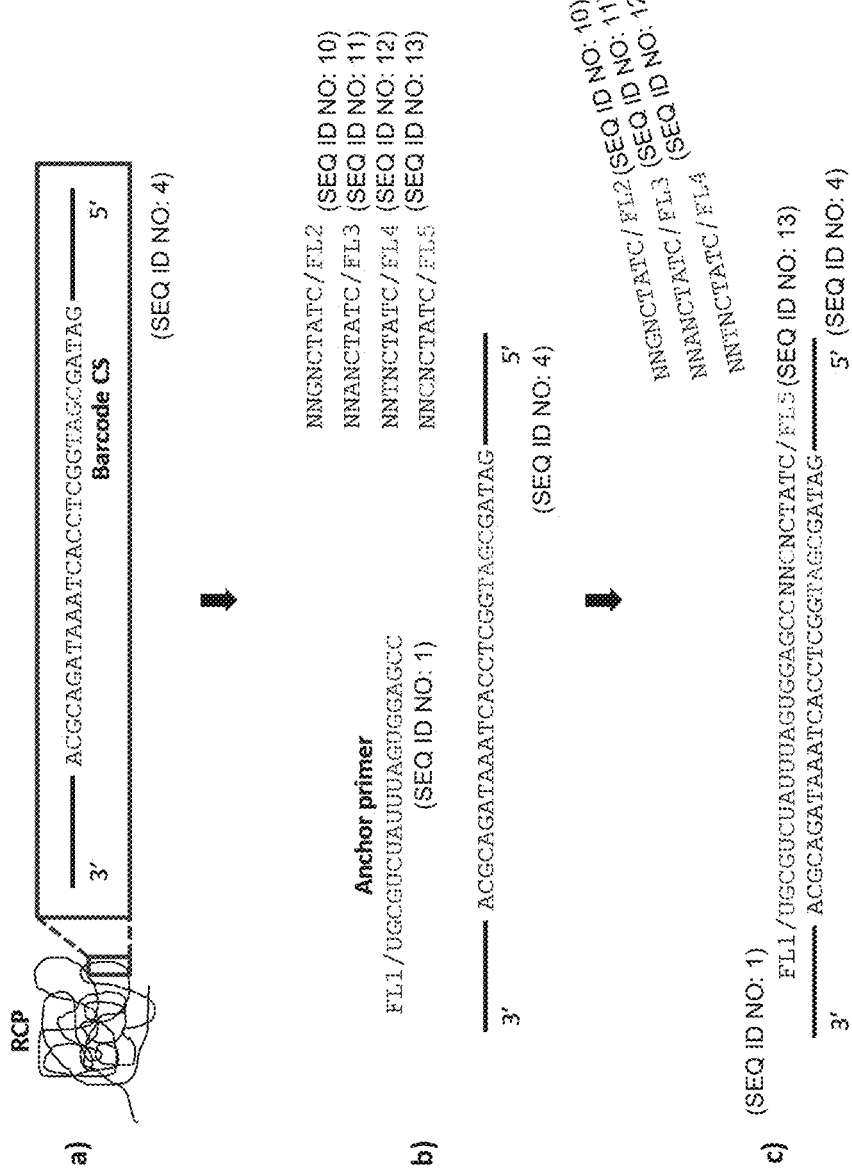
FIG. 9 schematically illustrates sequencing by hybridization (SBH) of a NAA generated by RCA to form a RCP. One sequencing cycle is depicted. The interrogation of guanine (G) at base position 3 of a TAGC barcode complementary sequence (barcode CS) is shown. a) RCPs contain multiple copies of the barcode CS. b) A fluorophore-labeled (FL1) anchor primer (to assist focusing) and fluorophore-labeled (FL2-FL5) 9-mer oligonucleotide probes that interrogate position 3 of the barcode CS are added. c) The anchor primer hybridizes to the complementary sequence in the RCP, upstream of the barcode CS. Individual oligonucleotide probes of the sequencing libraries interrogate the barcode CS. Perfectly matching probes exhibit a higher on-rate than partially mismatched oligonucleotide probes.

The present embodiments generally relate to nucleic acid sequencing, and in particular to such nucleic acid sequencing performed based on time-resolved measurements.

The present embodiments have thereby taken a radically different approach as compared to prior art sequencing methods relying on the incorporation, hybridization or ligation of labeled oligonucleotides, such as sequencing by ligation (SBL) or sequencing by hybridization (SBH). The prior art sequencing methods involve comparatively long incubation and reaction times in order to achieve sufficient incorporation, hybridization or ligation of the labeled oligonucleotides in order to distinguish correct specific labeling from unspecific background. These sequencing methods all rely on so called end-point measurements, i.e., performing label measurements once the long incubation and reaction periods have past. In addition, they typically involve a single measurement at a single point in time following the reaction and incubation, and subsequent washing.

The present embodiments are instead based on time-resolved measurements. This means that multiple, i.e., at least two, label measurements are performed and the results from the multiple measurements are co-processed in order to determine a sequenced base.

Such time-resolved measurements are generally significantly faster than the prior art sequencing methods since the measurements are performed during the actual incorporation, hybridization or ligation reaction. Accordingly, it is not necessary to await the end of any incubation and reaction period. In addition, it is not necessary to perform removal and washing steps prior to performing the time-resolved measurements. The present embodiments thereby speeds up and simplifies the sequencing as compared to prior art SBL and SBH methods.

The present embodiments may also improve the accuracy of nucleic acid sequencing. The reason being that sequencing methods based on end-point measurements are limited by false read errors that can occur due to misinterpretation of, for instance, auto fluorescence and clusters of fluorescently labeled oligonucleotides as sequence specific signals, or due to unspecific incorporation of fluorescently labeled oligonucleotides. The co-processing of multiple measurements performed during the reaction reduces the risk of such false read errors.

FIG. 1 is a flow diagram illustrating a nucleic acid sequencing method according to an embodiment. The method comprises contacting, in step S1, a spatially defined, at a spatially defined site, target nucleic acid sequence with N≥1 oligonucleotide probes. If N=1, the oligonucleotide probe has a label. If N≥2, each oligonucleotide probe of the N oligonucleotide probes has a nucleic acid sequence that is different from nucleic acid sequences of the other N–1 oligonucleotide probes of the N oligonucleotide probes. In addition, if N≥2, the N oligonucleotide probes have different labels or an oligonucleotide probe of the N oligonucleotide probes lacks a label and the other N–1 oligonucleotide probes of the N oligonucleotide probes have different labels.

A following step S2 comprises performing measurements at least at the spatially defined site at M≥2 time instances during i) a hybridization reaction comprising hybridization of the N oligonucleotide probes to the target nucleic acid sequence or ii) a ligation reaction comprising ligation of the N oligonucleotide probes to an anchor probe complementary to a segment of a nucleic acid molecule comprising the target nucleic acid sequence to form M data sets.

The M data sets are co-processed in step S3 in order to identify a label or absence of any label at the spatially defined site. The method further comprises determining, in step S4, a sequenced base of the target nucleic acid sequence based on the identified label or the identified absence of any label.

In a particular embodiment, step S4 comprises determining a sequenced base of the target nucleic acid sequence based on an increased presence of one of the identified label at the spatially defined site or a decreased or lack of presence of any label at the spatially defined site. Thus, identification of a label at the spatially defined site could be performed by identifying increased presence of a label at the spatially defined site. Thus, as time progresses the oligonucleotide probe that best matches the interrogated portion of the target nucleic acid sequence will be more present, i.e., at a higher number or local concentration, at the spatially defined site as compared to non-matching oligonucleotide probes.

The nucleic acid sequencing method of the embodiments can be used to sequence a base of any target nucleic acid sequence. The target nucleic acid sequence could comprise naturally occurring nucleotides, such as in a naturally occurring or a synthetic nucleic acid sequence, for instance in the form of a deoxyribonucleic acid (DNA) sequence, a ribonucleic acid (RNA) sequence or a complementary DNA (cDNA) sequence. The target nucleic acid sequence may, alternatively, comprise or consist of nucleic acid analogues and/or artificial or synthetic nucleotides, such as peptide nucleic acid (PNA), locked nucleic acid (LNA), glycol nucleic acid (GNA) and threose nucleic acid (TNA).

As is further described herein, the target nucleic acid sequence could be present in an isolated nucleic acid molecule, in a synthetic carrier or even within cells or tissue.

In an embodiment, step S2 comprises performing light measurements at least at the spatially defined site at $M \geq 2$ time instances during i) a hybridization reaction comprising hybridization of the N oligonucleotide probes to the target nucleic acid sequence or ii) a ligation reaction comprising ligation of the N oligonucleotide probes to an anchor probe complementary to a segment of a nucleic acid molecule comprising the target nucleic acid sequence to form M data sets.

The target nucleic acid sequence is spatially defined at a spatially defined site. This means that the position of the target nucleic acid sequence is spatially defined at the spatially defined site. Accordingly, when performing the (light) measurements it is possible to define, determine or identify the detected light or signal originating from the spatially defined site of or containing the target nucleic acid sequence and thereby determine or identify the detected light or signal originating from background, i.e., outside of the spatially defined site. This is schematically illustrated in FIG. 7 showing a spatially defined site 1 comprising the target nucleic acid sequence and an outside area 2 lacking any or lacking any significant amount of the target nucleic acid sequence. Accordingly, detected light or signal from the spatially defined site 1 originates from the measurements performed on the target nucleic acid sequence that is spatially defined at this site 1. Correspondingly, detected light or signal from the outside area 2 originates from background measurements.

FIG. 7 showing the outside area 2 surrounding the spatially defined site 1 is merely an example of how to detect light or signal originating from background. It can alternatively be measured at a completely different location or can be the average of several pixels within a defined area or the average of a few random pixels that are not part of the spatially defined site 1 that comprises the target nucleic acid sequence.

In an embodiment, step S1 comprises contacting the target nucleic acid sequence immobilized at the spatially defined site 1 with the N oligonucleotide probes. In this embodiment, the spatial definition of the target nucleic acid sequence at the spatially defined site 1 is achieved by immobilizing the target nucleic acid sequence at the spatially defined site 1.

FIG. 5 is a flow chart illustrating an additional, optional step of the method in FIG. 1 illustrating an embodiment of immobilizing the target nucleic acid sequence. In this embodiment, the method comprises immobilizing, in step S30, a nucleic acid molecule comprising the target nucleic acid sequence or hybridized to a nucleic acid molecule comprising the target nucleic acid sequence onto a solid support to form the spatially defined target nucleic acid sequence at the spatially defined site.

This embodiment thereby involves immobilizing a nucleic acid molecule onto a solid support. The immobilization can be achieved according to various embodiments including covalently binding the nucleic acid molecule onto the solid support, other forms of chemical bonding, such as ionic bonding the nucleic acid molecule onto the solid support, or passive forms of immobilization, such as absorbing the nucleic acid molecule onto the solid support.

For instance, the solid support can have a positively charged surface, such as poly-L-lysine coated surface, silanization of the surface with, for instance, an aminosilane, or coating the surface with other positively charged substances. Another technique for immobilization is to use biotin-avidin or biotin-streptavidin bonds. In such a case, the nucleic acid molecule comprises a biotin tag, or an avid or streptavidin tag, whereas the solid support is coated with avidin or streptavidin molecules, or biotin molecules.

Alternatively, the solid support can contain immobilized oligonucleotides, which comprise a complementary sequence to a part within the target nucleic acid molecule so that target nucleic acid molecules are captured to the solid support through hybridization. The solid support could also comprise porous material, such as membranes, polymers and pillars, in which target nucleic acid molecules are passively adsorbed, such as through diffusion, or actively captured, such as through electrophoretic forces or liquid flow through the membrane.

The solid support could be any solid support that can be used to immobilize the nucleic acid molecule and that is compatible with the (light) measurements. Non-limiting examples of such solid supports include glass supports, such as cover slips, and plastic supports, such as plastic wells or dishes. Another type of solid supports that can be used according to the embodiments is beads, such as polymer, gel, or magnetic beads.

In a first embodiment, the nucleic acid molecule comprises the target nucleic acid sequence. In such a case, the target nucleic acid sequence may constitute the complete sequence of the nucleic acid molecule. Alternatively, the nucleic acid molecule may comprise other nucleotides in addition to the target nucleic acid sequence. For instance, the nucleic acid molecule could be a carrier, such as plasmid, another circular carrier, or a non-circular carrier comprising the target nucleic acid sequence. In this first embodiment, the nucleic acid molecule is preferably an isolated nucleic acid molecule. In this first embodiment, the nucleic acid molecule with the target nucleic acid sequence is immobilized onto the solid support.

In a second embodiment, the nucleic acid molecule immobilized onto the solid support is hybridized to a nucleic acid molecule comprising the target nucleic acid sequence. Hence, in this embodiment, the nucleic acid molecule comprising the target nucleic acid sequence is not directly immobilized onto the solid support but is hybridized to another nucleic acid molecule that is directly immobilized onto the solid support. The nucleic acid molecule thereby comprises the target nucleic acid sequence and a sequence complementary to at least a portion of the sequence of another nucleic acid molecule immobilized onto the solid support.

In another embodiment, step S30 of FIG. 5 comprises immobilizing a nucleic acid molecule comprising the target nucleic acid sequence in a gel matrix to form the spatially defined target nucleic acid sequence at the spatially defined site.

This embodiment thereby utilizes a gel matrix, preferably a three dimensional (3D) gel matrix, entrapping the nucleic acid molecule. This embodiment is particularly suitable for sequencing target nucleic acid sequences within cells, tissues or other biological specimen. In a particular embodiment, the cells or tissue is first embedded into the gel matrix and the nucleic acid molecule may optionally be crosslinked onto the matrix of the gel while preserving the spatial positioning within the cell or tissue specimen. Optionally, the biological material may then be removed from the gel matrix, while the nucleic acid molecules are left behind in their spatially defined positions within the gel matrix.

This embodiment of immobilizing nucleic acid molecules may also be used for isolated nucleic acid molecules, i.e., the nucleic acid molecules do not necessarily have to be within a biological specimen, such as cells or tissue. For instance, the gel can be used to replace the biological material and embedding the target nucleic acid sequence into a gel matrix, thereby preserving its spatial location.

Alternatively, target nucleic acid molecules can be formed in, or embedded into gel matrices randomly. For instance, nucleic acid molecules in liquids can be mixed with a gel or gel forming material. In such an approach, target nucleic acid sequences will be randomly distributed within the gel matrix at spatially defined locations.

It is also possible that the target nucleic acid sequence is attached to, such as bound to, some form of binder to achieve the immobilization. Non-limiting, but illustrative examples of such binders could be an aptamer, a protein, an antibody, etc. For instance, the nucleic acid sequencing method can be applied to multiplexing protein detection by sequencing barcodes in the protein-nucleic acid tags.

The nucleic acid sequencing method of FIG. 1 employs, as mentioned in the foregoing, at least one labeled oligonucleotide probe. In a first embodiment N is equal to one, i.e., using one labeled oligonucleotide probe. This embodiment is particularly suitable when conducting the nucleic acid sequencing method serially in cycles. For instance, the labeled oligonucleotide probe could be used to interrogate at least one base in the target nucleic acid sequence. M (light) measurements are performed in step S2 at least at the spatially defined site and the resulting M data sets are co-processed in step S3. If the co-processing of the M data sets leads to detection of the labeled oligonucleotide probe at the spatially defined site then the at least one base in the target nucleic acid sequence corresponding to at least one probing complementary base in the labeled oligonucleotide probe is determined. If the co-processing of the M data sets, however, leads to no detection of the labeled oligonucleotide probe at the spatially defined site, then the method steps S1 to S4 could be repeated at least once but with another labeled oligonucleotide probe. This another labeled oligonucleotide probe has at least one different probing complementary base as compared to the previously used labeled oligonucleotide probe.

Hence, in this approach a single type of oligonucleotide probe is tested per cycle until the co-processing in step S3 reveals the presence of the labeled oligonucleotide probe at the spatially defined site and at least one base of the target nucleic acid sequence can be determined.

Generally, if one base is to be sequenced then at most three cycles need to be performed with different probes. For instance, the labeled oligonucleotide probe in the first cycle could have A (or T/U, G or C) as probing complementary base, the labeled oligonucleotide probe in the second cycle could have T or U (or G, C or A) as probing complementary base and the labeled oligonucleotide probe in the third cycle could have G (or C, A or T/U) as probing complementary base. For instance, if the co-processing of the M data sets from the second cycle defines identification of the labeled oligonucleotide probe in the spatially defined site then the sequenced base is determined by be A. If no labeled oligonucleotide probe is identified following the first to third cycle, then one can conclude that the sequenced base will be C in the above presented example. It is of course possible to have a fourth cycle with a labeled oligonucleotide probe having C (or A, T/U or C) as probing complementary base to verify that the sequenced base is C.

The oligonucleotide probes used in the different cycles preferably have different labels in order to distinguish the oligonucleotide probes from each other. However, this is not absolutely necessary. In such a case, a same label can be used for each oligonucleotide probe.

The above described embodiment thereby uses only a single type of labeled oligonucleotide probe per cycle in the reaction mixture. A drawback with this embodiment is that several cycles, up to at least three, might be needed in order to determine a sequenced base in the target nucleic acid sequence.

Other embodiments as further described below can determine the sequenced base in a single cycle and are thereby even faster than the above described embodiment.

Note that the determination in step S4 or the determination in step S4 and the co-processing in step S3 does not necessarily have to be performed in connection with each cycle. In clear contrast, steps S1 to S2 or S1 to S3 could be performed once for each cycle and then the resulting M data sets from each cycle are co-processed in order to determine a sequenced based on the identification of presence of the particularly labeled oligonucleotide probe. This approach enables performing all experiments and measurements first and then perform the data processing at a later stage.

In another embodiment, N is equal to or larger than 2. In such an embodiment, each oligonucleotide probe of the N oligonucleotide probes has a nucleic acid sequence that is different from nucleic acid sequences of the other N−1 oligonucleotide probes of the N oligonucleotide probes. The N oligonucleotide probes thereby have different probing complementary base(s) that is(are) used to probe one or more base positions in the target nucleic acid sequence. This means that the N oligonucleotide probes may have at least one portion that is common for all oligonucleotide probes and one portion that is unique for each oligonucleotide probe. For instance, four oligonucleotide probes could have the following sequences $NA(N)_x$, $NT(N)_x$, $NG(N)_x$, $NC(N)_x$, wherein x is a positive number preferably equal to or larger than two and N is any of A, T/U, G and C, in order to probe a second base position in the target nucleic acid sequence.

In an embodiment, the N oligonucleotide probes have different labels. This means that the oligonucleotide probe of a first type, i.e., having a first nucleic acid sequence, has a first label, the oligonucleotide probe of a second type, i.e., having a second, different nucleic acid sequence, has a second, different label, and so on.

In such a case, the sequenced base is determined in step S4 based on the particular label and thereby labeled oligonucleotide probe identified at the spatially defined site. For instance, if the co-processing of the M data set identifies the second label in the spatially defined site and this label is present in the oligonucleotide probes having the sequence NT(N)$_x$ then the sequenced based of the target nucleic acid sequence is determined to be A.

In another embodiment, one of the oligonucleotide probes lacks any label, whereas the remaining N−1 oligonucleotide probes have different labels. In such a case, the sequenced base is determined in step S4 based on the particular label identified at the spatially defined site or based on the absence of any identified label at the spatially defined site.

In a particular embodiment, step S1 comprises contacting the spatially defined, at the spatially defined site, target nucleic acid sequence with four oligonucleotide probes. Each oligonucleotide probe of the four oligonucleotide probes has a nucleotide at a specific base position of the four oligonucleotide probes that is different from a nucleotide at the specific base position of the other three oligonucleotide probes. This embodiment enables probing the sequenced base position in the target nucleic acid sequence in a single cycle using four different oligonucleotide probes, one having A at the specific base position, another having T/U at the specific base position, a third having G at the specific base position and the fourth having C at the specific base position.

In this embodiment, the four different oligonucleotide probes may have different labels or three of the four different oligonucleotide probes may have different labels and the remaining oligonucleotide probe lacks any label.

Figure 10:
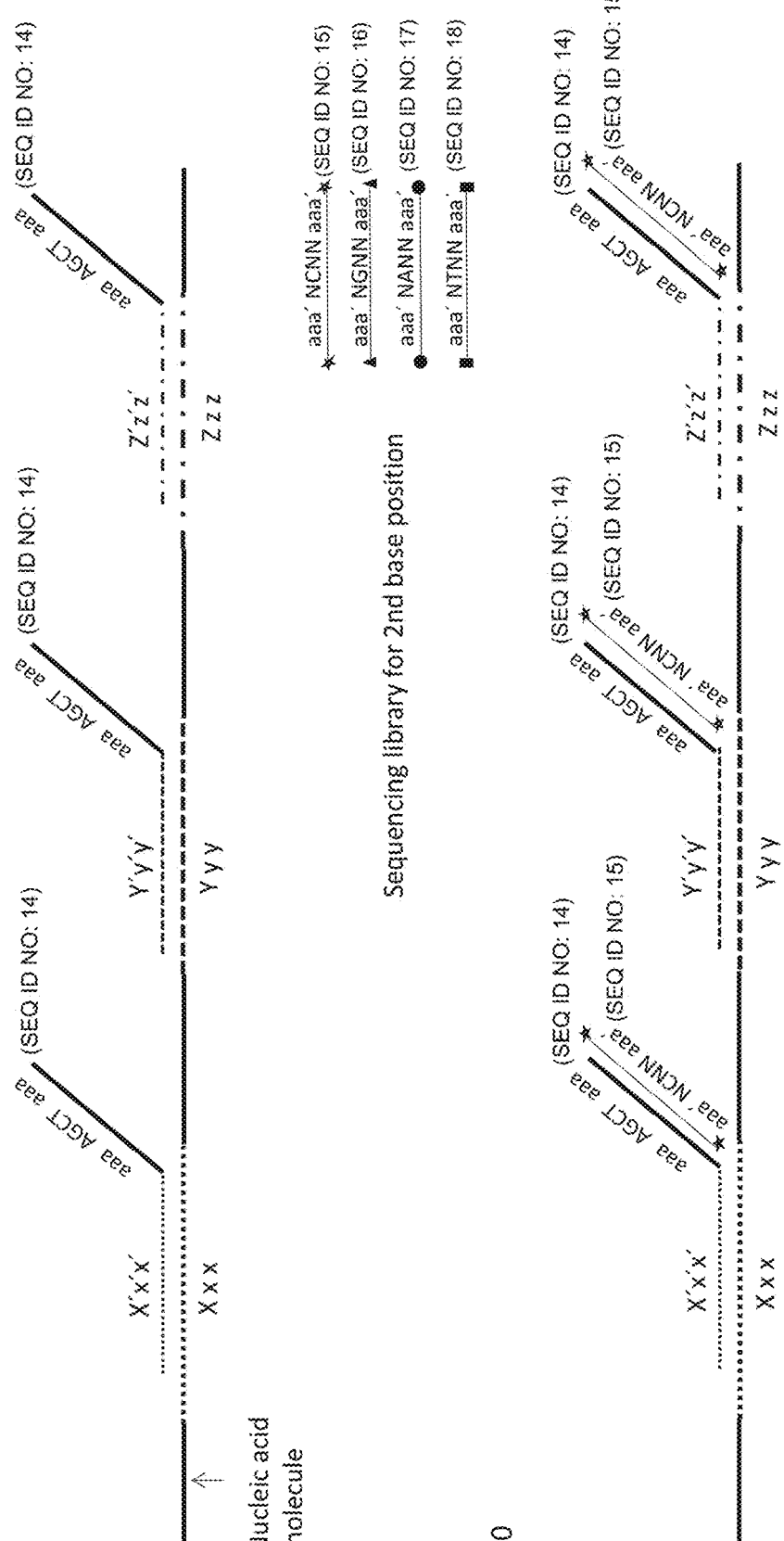
FIG. 10 illustrates NAA generated through concerted hybridization probes on individual nucleic acid molecules. Hybridization probes comprise a respective complementary sequence and a non-hybridizing common overhang sequence with a barcode sequence that is unique for the identified nucleic acid molecule, and common for all hybridization probes hybridizing to the same nucleic acid molecule.

Alternatively, one of the oligonucleotide probes may have either one or another label so that the target nucleic acid sequence, if consisting of multiple target nucleic acid sequence strands, see FIG. 10, is labeled with two labels at the same time, which identifies the base which the oligonucleotide probe that is labeled with either one of the two labels identifies. In this approach, a portion of the first oligonucleotide probes has a first label and a remaining portion of the first oligonucleotide probes has a second, different label.

Another possibility of performing sequencing of a base position in the target nucleotide acid sequence in a single cycle is to use three different oligonucleotide probes having three different labels. If the co-processing identifies one of the labels at the spatially defined position then the nucleotide complementary to the nucleotide at its specific base position is the nucleotide at the sequenced base position. If none of the three different labels is identified at the spatially defined position, then the nucleotide complementary to the fourth remaining nucleotide not present in the specific base position of any of the three oligonucleotide probes is the nucleotide of the sequenced base position.

It is possible to probe more than one base position in the target nucleic acid sequence per cycle. For instance, 16 oligonucleotide probes could be used to probe two base position, such as having the respective sequences NAA(N)$_x$, NAT(N)$_x$, NAG(N)$_x$, NAC(N)$_x$, NTA(N)$_x$, NTT(N)$_x$, NTG(N)$_x$, NTC(N)$_x$, NGA(N)$_x$, NGT(N)$_x$, NGG(N)$_x$, NGC(N)$_x$, NCA(N)$_x$, NCT(N)$_x$, NCG(N)$_x$ or NCC(N)$_x$.

Thus, the embodiments are not limited to sequencing a single base or base position per cycle but could sequence multiple bases or base positions in the target nucleic acid sequence per cycle.

The nucleic acid sequencing method performs (light) measurements at least twice at least at the spatially defined site. Experimental data as presented herein indicate that it is possible to identify presence of a label or absence of a label at the spatially defined site already after two measurement points. In some cases, the accuracy in the determination is improved if M is at least 3, such as at least 4 or at least 5. Hence, in a preferred embodiment, the (light) measurements in step S2 are performed at M≥3, M≥4 or M≥5 time instances to form the M data sets.

In an embodiment, step S2 comprises performing measurements, such as light measurements, at least at the spatially defined site at M≥2 time instances separated from each other with at least 20 ns during i) the hybridization reaction comprising hybridization of the N oligonucleotide probes to the target nucleic acid sequence or ii) the ligation reaction comprising ligation of the N oligonucleotide probes to the anchor probe complementary to the segment of the nucleic acid molecule comprising the target nucleic acid sequence to form the M data sets.

Step S2 could be performed according to various embodiments. In a first embodiment, M time-resolved (light) measurements are performed at least at the spatially defined site to get the M data sets. For instance, M time-resolved images can be taken in step S2 of at least the spatially defined site with an inter-image capture time of, preferably, at least 20 ns to form M image data sets. In such an embodiment, step S3 comprises co-processing the M image data sets in order to identify a label or absence of any label at the spatially defined site.

In a second embodiment, the (light) measurements could be performed using comparatively long exposure times, similar to recording video. In such a case, each data set of the M data sets comprises (light) detection data of one frame or image in the recorded video or long exposure (light) measurement. This embodiment thereby involves retrieving or extracting M frames or images or videos from the measurement data to obtain the M data sets.

In an embodiment, the (light) measurements are performed at M time instances separated from each other with at least 20 ns. This preferred lower limit of 20 ns corresponds to the time period for hybridization kinetics, i.e., hybridization and dehybridization of oligonucleotide probes to the target nucleic acid sequence.

Although 20 ns is a preferred lowest limit with regard to performing (light) measurements, the present embodiments may use longer time intervals between the M time instances, such as time intervals in the μs range, in the ms range, or in the s range. The time interval may even be up to in the min range although shorter time interval are generally preferred. For instance, the time interval could be selected to correspond to the time period for relocation of labels between pixel or voxel (volume element) positions due to Brownian motion and hybridization kinetics. Thus, the time interval could be selected to allow a label to move from a first detectable spatial position (pixel or voxel position) to another detectable spatial position. This time interval is dependent on the pixel or voxel size, and thereby resolution of microscope or detection equipment.

It is also possible to use a shorter limit than 20 ns. Hence, the M time instances separated from each with less than 20 ns.

Please note that it is not necessary to use the same time interval between each (light) measurement. For instance, the time interval between the first and second (light) measurement may be different from the time interval between the second and the third (light) measurement.

Generally, the shorter the time interval between the (light) measurements, the more measurement time instances are preferably used, i.e., larger M. Correspondingly, the longer the time interval between the (light) measurements, the fewer measurement time instances, i.e., smaller M, may be need in order to determine a sequenced base.

In an embodiment, step S2 of FIG. 1 comprises measuring fluorescence, at least at the spatially defined site, at the M time instances, such as separated from each other with at least 20 ns, to form M fluorescence data sets.

In this embodiment, the labels of the oligonucleotide probes are preferably fluorescent labels, e.g., fluorophores.

In a particular embodiment, step S2 comprises measuring fluorescence intensity in a) N or b) N−1 fluorescence channels. In a), each fluorescence channel of the N fluorescence channels corresponds to a wavelength of a respective fluorescent label of the N oligonucleotide probes. In b), each fluorescence channel of the N−1 fluorescence channels corresponds to a wavelength of a respective fluorescent label of the other N−1 oligonucleotide probes. Thus, a) is used if each oligonucleotide probe has a respective fluorescent label and b) is used if one of the oligonucleotide probes lacks a fluorescent label but the other N−1 oligonucleotide probes has a respective fluorescent label.

Although fluorescent labels are preferred examples of labels that could be used in the oligonucleotide probes, the embodiments are not limited thereto. Alternatively, non-fluorescent labels could be used. Non-limiting, but illustrative examples, of such non-fluorescent labels include colorimetric labels, such as using colorimetric nanoparticles, e.g., cellulose or latex nanobeads. Such colorimetric labels or nanoparticles could then absorb light of different wavelengths and thereby be used to identify presence or absence of labels and oligonucleotide probes at the spatially defined site. Other labels that could be detected in light measurements include, for instance, gold or silver particles that can be detected by bright field (BF) imaging, quantum dots, organic fluorophores, fluorescent proteins, such as green fluorescent protein (GFP), etc.

The co-processing of the M data sets in step S3 can be performed according to various embodiments. In a first embodiment, see FIG. 2, the method continues from step S2 in FIG. 1. A next step S10 comprises generating, i) if N=1, for the oligonucleotide probe, or if N≥2, iia) for each oligonucleotide probe of the N oligonucleotide probes or iib) for each oligonucleotide probe of the N−1 oligonucleotide probes having labels, a combined data set of selected intensity projections from the M data sets. A next step S11 comprises identifying the label or the absence of any label at the spatially defined site based on the combined data set. The method then continues to step S4 in FIG. 1.

In this embodiment, the M data sets are co-processed by generating a combined data set of selected intensity projections. This could, in an embodiment, be achieved by, for each pixel or voxel position in the combined data set, i.e., each detectable position in at least the spatially defined site, select one intensity projection from the M data sets. For instance, the combined data set could include minimum or maximum intensity projections, i.e., minimum or maximum intensity values from the M data sets. This would correspond to generating a combined data set $cds_{ij}=\min(k_{ij})$ or $cds_{ij}=\max(k_{ij})$, wherein $cds_{ij}$ represents an intensity projection or value at pixel position (i, j) in the combined data set, $k_{ij}$ represents an intensity projection or value at pixel position (i, j) in data set k, k=1 . . . M, min(.) is a min function returning the smallest value and max(.) is a max function returning the largest value.

In another embodiment, step S10 comprises generating, i) if N=1, for the oligonucleotide probe, or if N≥2, iia) for each oligonucleotide probe of the N oligonucleotide probes or iib) for each oligonucleotide probe of the N−1 oligonucleotide probes having labels, a combined data set by summing intensity projections from the M data sets. A next step S11 comprises identifying the label or the absence of any label at the spatially defined site based on the combined data set.

In this embodiment, the M data sets are co-processed by generating a combined data set of the sum, in each pixel or voxel position, of the respective intensity projections or values of that pixel position in the M data sets. This would correspond to generate a combined data set $cds_{ij}=\Sigma_{k=1}^{M} k_{ij}$.

In yet another embodiment, step S10 comprises generating, i) if N=1, for the oligonucleotide probe, or if N≥2, iia) for each oligonucleotide probe of the N oligonucleotide probes or iib) for each oligonucleotide probe of the N−1 oligonucleotide probes having labels, a combined data set by averaging intensity projections from the M data sets. A next step S11 comprises identifying the label or the absence of any label at the spatially defined site based on the combined data set.

In this embodiment, the M data sets are co-processed by generating a combined data set of the average, in each pixel or voxel position, intensity projection or value of the M data sets. This would correspond to generate a combined data set $$cds_{ij} = \frac{\sum_{k=1}^{M} k_{ij}}{M}.$$

In an embodiment, step S2 of FIG. 1 comprises performing (light) measurements, at the spatially defined site 1, see FIG. 7, and outside 2 of the spatially defined site 1, at the M time instances to form the M data sets. The method then continues to step S10, which comprises generating a combined data set according to any of the above described embodiments. The method then continues to step S12 in FIG. 3. This step S12 comprises calculating, for each combined data set of the combined data sets, a quotient between intensity values at the spatially defined site 1 and intensity values outside 2 of the spatially defined site 1. A following step S13 comprises identifying the label or the absence of any label based on the quotients.

The quotient is thereby calculated as $I_1/I_2$, wherein $I_1$ represents the intensity values at the spatially defined site 1 and $I_2$ represents intensity values outside 2 of the spatially defined site 1. In an embodiment, $I_1$ represents the average intensity value of the combined data set within the spatially defined site 1 and $I_2$ represents the average intensity value of the combined data set outside 2 of the spatially defined site 1. Other variants for determining $I_1$ and $I_2$ include median intensity value or sum of intensity values within the spatially defined site 1 and outside 2 of the spatially defined site 1, respectively.

FIG. 4 illustrates another embodiment of calculating quotients. In this embodiment, step S2 in FIG. 1 comprises performing the (light) measurements, at the spatially defined site 1 and outside 2 of the spatially defined site 1, at the M time instances to form the M data sets. The method then continues to step S20 in FIG. 4. This step S20 comprises calculating, for each data set of the M data sets, a quotient between intensity values at the spatially defined site 1 and intensity values outside 2 of the spatially defined site 1. A next step S21 comprises identifying the label or the absence of any label based on the quotients. The method then continues to step S4 in FIG. 1.

Each quotient is thereby calculated as $I_1/I_2$, wherein $I_1$ represents the intensity values at the spatially defined site 1 and $I_2$ represents intensity values outside 2 of the spatially defined site 1 for the current data set. In an embodiment, $I_1$ represents the average intensity value of the current data set within the spatially defined site 1 and $I_2$ represents the average intensity value of the current data set outside 2 of the spatially defined site 1. Other variants for determining $I_1$ and $I_2$ include median intensity value or sum of intensity values within the spatially defined site 1 and outside 2 of the spatially defined site 1, respectively.

Such a quotient between $I_1/I_2$ is preferably calculated for each labeled oligonucleotide probe thereby resulting in N or N−1 such quotients per interrogated or probed base position in the target nucleotide sequence.

Thus, the co-processing of the embodiments could be performed according to various embodiment. For instance, all the images of a time stack could be integrated. It is also possible to process all time data sets from the different channels, e.g., one channel per label, simultaneously. It is, though, also possible to process them one after another.

The nucleic acid sequencing method of the embodiments may advantageously be used in connection with sequencing by ligation in order to achieve a time-resolved sequencing by ligation (tr-SBL). In such an approach, step S1 of FIG. 1 preferably comprises contacting the spatially defined, at the spatially defined site, target nucleic acid with the N oligonucleotide probes in presence of a ligating enzyme and an anchor probe complementary to a segment of a nucleic acid molecule comprising the target nucleic acid sequence. The segment in the nucleic acid molecule is adjacent the target nucleic acid sequence.

FIG. 8 schematically illustrates this approach. FIG. 8A illustrates the nucleic acid molecule comprising a barcode complementary sequence (barcode CS) CGTA that corresponds to the target nucleic acid sequence to be sequenced. FIG. 8B illustrates a labeled anchor probe or primer having a sequence that is complementary to a segment of the nucleic acid molecule adjacent to, in this example upstream of, the barcode complementary sequence. FIG. 8B also illustrates four oligonucleotide probes each having a respective fluorescent label (FL2-FL5). Each oligonucleotide probe has a random nucleotide N, a respective first nucleotide (G, A, T or C) followed by two random nucleotides NN and a common motif CTATC that is complementary to a portion of the nucleic acid sequence. These oligonucleotide probes are designed to interrogate the second base position of the barcode complementary sequence.

The anchor primer hybridizes to the complementary sequence of the nucleic acid molecule as shown in FIG. 8C. Sequencing by ligation relies upon the sensitivity of a ligase for base-pairing mismatches. The barcode to be sequence is flanked on at least one end by a known sequence, to which the anchor primer is complementary and hybridizes. A mixed pool of labeled oligonucleotide probes is then added and allowed to hybridize to the barcode complementary sequence, next to the anchor primer and the ligase preferentially joins the oligonucleotide probe to the anchor primer when its bases match the barcode complementary sequence as shown in FIG. 8C.

Generally, sequencing by ligation can proceed in either direction, i.e., 5'→3' or 3'→5', depending on to which end of the oligonucleotide probe the label is bound.

The ligating enzyme used in the tr-SBL is preferably a ligase, such as a DNA ligase. Non-limiting examples of such DNA ligase include *Escherichia coli* DNA ligase, T4 DNA ligase, *Thermus thermophilus* DNA ligase, Taq DNA ligase, DNA ligase I, DNA ligase III and DNA ligase IV, preferably T4 DNA ligase or *Thermus thermophilus* DNA ligase.

In SBL, accumulation of matching oligonucleotide probes in the target nucleic acid sequence is mediated by hybridization and enzymatic ligation of, preferably fluorescently, labeled oligonucleotide probes to a juxtaposed longer oligonucleotide of known sequence, denoted anchor probe or primer, see FIG. 8.

Compared to SBH, SBL increases accumulation of matching oligonucleotide probes to the target nucleic acid sequence by ligation of the short oligonucleotide probes to the longer anchor probe and, thus, locking it onto the anchor probe, which considerably decreases the off-rate of the probe complex. The strong competition of oligonucleotide probes competing for the same hybridization position facilitates that mostly the correct matching oligonucleotide probes become ligated to the anchor probe. With increasing SBL reaction time the correct matching oligonucleotide probe concentration in the spatially defined site increases.

In the prior art, after washing and end-point measurement mostly the correct oligonucleotide probes are present so that end-point measurements are sufficient to perform accurate sequencing. Long reaction times, typically 30-60 min, are required in order to significantly increase the accumulation of the correct oligonucleotide proves in in the target nucleic acid sequence.

Figure 13:
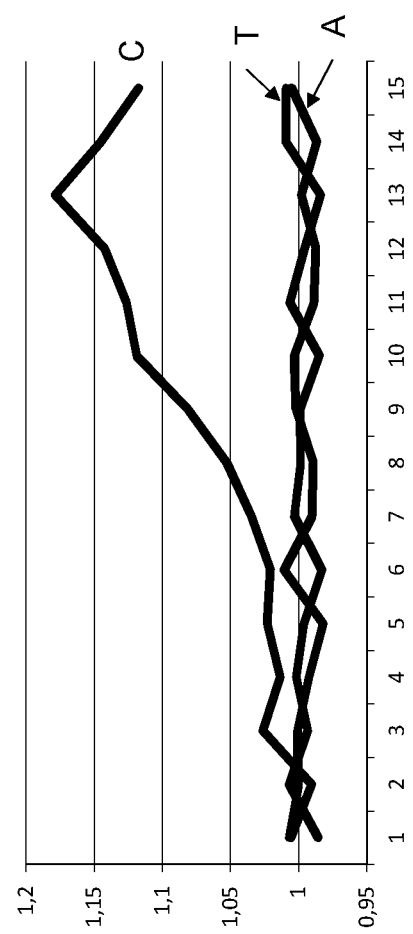
FIG. 13 illustrates the results of a SBL experiment. The diagram illustrates signal to noise ratio of average pixel intensity inside a defined RCP and averaged background around one RCP. X axis: arbitrary time units: time point 5 is 3.20 min. The anchor primer stained a RCP prior to the real time measurement, to which the sequencing library (A, C or T) was ligated. True complementary signal is base C. The base C can be called already from time point 6 or 7. Note: The library specific for guanine (G) has been omitted from the reaction since the fluorophore is used for anchor primer labeling.

In tr-SBL, an interrogated base can be called as soon as the intensity of one fluorescent label within the spatially defined site reaches a certain threshold. In addition to the accumulation of fluorescent labels in the spatially defined site over time, due to increasing ligation of oligonucleotide probes over time, the fluorescent signals in the target nucleic acid sequence and the spatially defined site are spatially fixed while fluorescent signals from free oligonucleotide probes, i.e., outside of the spatially defined site, fluctuate over time. Integrating the time dimension, the fluorescence intensity values of pixels or voxels (volume elements), that contain the target nucleic acid increase as shown in FIG. 13, while pixel or voxel values of background stay stable or fluctuate over time. Hence, multiple frames or images analysis during the sequencing reaction enables discerning a target nucleic acid sequence from background already before the fluorescence intensity of the target nucleic acid sequence (spatially defined site) exceeds that of the background. This facilitates detecting the sequenced base before it actually becomes visible in an end-point measurement.

Tr-SBL drastically increases reaction speed of SBL reactions from up to 60 min to less than 10 min. Moreover, tr-SBL increases the accuracy. In end-point measurements, any staining artifacts that occur with size and intensity range of target nucleic acid sequences, will be taken into account and can contribute to a decrease in sequencing accuracy. The real time measurement of the sequencing reaction, however, enables discarding objects that suddenly appear during the reaction or objects that have a bright fluorescence from the very start of the reaction, e.g., autofluorescent foci or random oligonucleotide clusters. This way, accuracy of target nucleic acid sequence identification and base sequencing during the sequencing reaction are increased.

The nucleic acid sequencing method of the embodiments may advantageously be used in connection with sequencing by hybridization in order to achieve a time-resolved sequencing by hybridization (tr-SBH).

The hybridization of one strand of DNA to its complementary strand in the DNA double-helix is sensitive to even single-base mismatches when the hybrid region is short or if specialized mismatch detection proteins are present. This is exploited in SBH.

FIG. 9 schematically illustrates this approach. FIG. 9A illustrates the nucleic acid molecule comprising a barcode complementary sequence (barcode CS) TAGC that corresponds to the target nucleic acid sequence to be sequenced.

FIG. 9B illustrates a labeled anchor probe or primer having a sequence that is complementary to a segment of the nucleic acid molecule, in this example upstream of, the barcode complementary sequence. FIG. 9B also illustrates four oligonucleotide probes each having a respective fluorescent label (FL2-FL5). Each oligonucleotide probe has two random nucleotides NN, a respective first nucleotide (G, A, T or C) followed by a random nucleotide N and a common motif CTATC that is complementary to a portion of the nucleic acid sequence. These oligonucleotide probes are designed to interrogate the third base position of the barcode complementary sequence.

The anchor primer hybridizes to the complementary sequence of the nucleic acid molecule to provide a focusing aid during imaging as shown in FIG. 9C. A mixed pool of labeled oligonucleotide probes is then added and allowed to hybridize to the barcode complementary sequence (CS), in this example next to the anchor primer as shown in FIG. 9C.

Generally, sequencing by hybridization can proceed in either direction, i.e., 5'→3' or 3'→5', depending on to which end of the oligonucleotide probe the label is bound.

FIG. 10 illustrates another approach. In this embodiment, step S1 of FIG. 1 comprises contacting the spatially defined, at the spatially defined site, target nucleic acid sequence with the N oligonucleotide probes in presence of a hybridization probe comprising i) a sequence complementary to a segment of an immobilized nucleic acid molecule and ii) the target nucleic acid sequence.

Thus, in this approach a nucleic acid molecule is immobilized onto a solid support as previously described herein. One or multiple different hybridization probes are then allowed to hybridize to a respective segment of the nucleic acid molecule. FIG. illustrates three such segments Xxx, Yyy and Zzz and thereby uses three different hybridization probes. In this example, each hybridization probe has a respective sequence complementary to one of the three segments and an overhang sequence that is common for all hybridization probes. This overhang sequence comprises the target nucleic sequence, represented by AGCT in FIG. 10.

FIG. 10 also illustrates four different labeled oligonucleotide probes that can be used to sequence the second base position of the target nucleic acid sequence in a tr-SBH reaction. The oligonucleotide probes can then hybridize to each target nucleic acid sequence in the overhang portion to thereby achieve an amplification of the fluorescence signal at the spatially defined site.

In tr-SBH, N oligonucleotide probes are allowed to hybridize to a target nucleic acid sequence. The oligonucleotide probes can be designed to carry the interrogation base proximal on either 3' or 5' end, or preferably in the middle of the oligonucleotide probe as shown in FIG. 10.

Tr-SBH can be used to sequence, for instance, barcode sequences, which can constitute a minimum of two nucleotides up to ten or more nucleotides that can code for a certain nucleic acid molecule. In FIG. 10, barcodes comprising four nucleotides are introduced into a nucleic acid molecule and are sequenced through sets of four oligonucleotide probes carrying interrogation sites for 4-nucleotides barcode sequences. The interrogation site is degenerated (N), which means any of the four bases (A, G, C, T) can be incorporated on that position, except for the base which is to be interrogated (base position 2 in FIG. 10). Each base on that position is then encoded by one (or two, or none) labeled oligonucleotide probes.

The oligonucleotide probes are then applied to the nucleic acid molecule and allowed to hybridize under specific conditions. Hybridization of oligonucleotide probes to the barcode sequences (target nucleic acid sequence) occurs nearly instantly and oligonucleotide probes start competing for hybridization to the barcode sequence. All oligonucleotide probes hybridize to barcode sequence to a certain extent, but oligonucleotide probes with a higher degree of sequence complementarity have a higher association constant, or higher hybridization on-rate, than mismatching oligonucleotide probes.

The length of the oligonucleotide probes and the buffer and temperature conditions are selected such that even perfectly matching oligonucleotide probes hybridize only transiently, but with a larger on-rate as compared to mismatching oligonucleotide probes. In addition to an increased accumulation of matching oligonucleotide probes in the spatially defined site as compared to mismatching oligonucleotide probes, the fluorescent signals of the matching oligonucleotide probes inside the spatially defined site are spatially fixed and do not fluctuate, while the fluorescent signals from free mismatching oligonucleotide probes fluctuate over time due to oligonucleotide probes diffusing in and out of the pixel or voxel position.

Integrating the time dimension in the image analysis, the fluorescence intensity values of pixels or voxels that contain the barcode sequences (spatially defined site) increase or stay stable, while corresponding fluorescence intensity values of background decrease or stay stable, and much lower, over time depending on image integration algorithm. Hence, multiple frames or images analysis during the sequencing reaction enables to discern a target nucleic acid sequence from the background. Target nucleic acid sequences are barely visible or not distinguishable in one image or frame during this process.

Tr-SBH increases the accuracy of the sequencing process compared to measuring SBH reactions with traditional end-point measurements. For end-point measurements, the sequencing reaction mixture is removed and then at least one washing step is performed to remove all unspecifically bound oligonucleotide probes. Due to the comparatively low affinity of the short oligonucleotide probes also correct fully matching oligonucleotide probes are removed during the washing step, which leads to an overall signal decrease. This can result in poor signal-to-noise ratios.

In tr-SBH, slight differences in affinity of oligonucleotide probes can be distinguished by integrating several measurements, which leads to a stronger increase in the quotient between intensity within the spatially defined site and intensity outside of the spatially defined site of the perfectly matching oligonucleotide probe over the number of measurements than oligonucleotide probes with mismatches as shown in FIG. 14B (base T). This may also facilitate distinguishing the right base even in more difficult sequences, i.e., with repetitive motifs (homologs), high GC content, or secondary structures. In end-point measurements, however, a slight difference in signal intensity between two oligonucleotide probes with nearly similar affinity would not be distinguishable, which leads to decreasing sequencing accuracy.

Moreover, in end-point measurements, any staining artifacts that occur with size and intensity range of target nucleic acid sequences, may be taken into account and can contribute to a decrease of sequencing accuracy. The real time measurement of the sequencing reaction, however, enables discarding objects that suddenly appear during the reaction or objects that have a bright fluorescence from the very start of the reaction, e.g., autofluorescent foci or random oligonucleotide clusters. This way, accuracy of target nucleic acid sequence identification and base calling during sequencing are increased.

Another advantage of tr-SBH is that the washing step(s) may be omitted, which decreases the number of method steps and time. With tr-SBH it is possible to simply remove the reaction mixture after the interrogated base is determined and replace it with the reaction mixture for the next base. No washing is needed in between because tr-SBH uses short oligonucleotide probes, which only transiently hybridize to the target nucleic acid sequence. After removing excess oligonucleotide probes in the reaction mixture, the oligonucleotide probe concentration from the previous sequenced base decreases drastically leading to a strong decline in the concentration-dependent association constant. The matching oligonucleotide probe for the next base is then in much higher concentration and out-competes the previous oligonucleotide probe. Tr-SBH is sensitive to this change by measuring the fluorescent signal change over time. Tr-SBH can be used to measure the kinetics of dissociation of one oligonucleotide probe and the association of the next oligonucleotide probe in individual target nucleic acid sequences. Since the kinetics are sequence dependent such measurements may be used for sequence interpretation and distinguishing target nucleic acid sequences.

The oligonucleotide probe is hybridized to the target nucleic acid sequence at a concentration optimized to permit detection of the locally increased concentration of the matching oligonucleotide probe hybridized onto the target nucleic acid sequence, over the fluctuating background in all the liquid. A single image does not allow detecting the hybridized target nucleic acid sequence because background may be higher, as high, or just slightly lower than the hybridization signature in the target nucleic acid sequence.

For example, 20 nM of each oligonucleotide probe may be used, or the oligonucleotide probe may be hybridized at 0.001 nM up to 5 µM depending on the optical setup. The reaction is then imaged at low exposure with multiple frames or images at different time points, instead of only one image. Through image integration of the multiple frames or images, the matching oligonucleotide probe can be detected above background and above hybridization of mismatching oligonucleotide probes. The advantage of this detection scheme is that it avoids washing steps, so that detection can proceed at equilibrium hybridization conditions, which facilitates match/mismatch discrimination. Moreover, after determining the hybridized matching oligonucleotide probe and, hence, the interrogated base, the hybridization mixture can simply be removed from the reaction chamber, such as flow cell, and replaced with the hybridization mixture for the next base, without need of washing. The concentration of the still hybridized matching oligonucleotide probe will then, by change to the new hybridization mixture, drastically decrease and increase the off-rate of this oligonucleotide probe to the target nucleic acid sequence. Eventually, after short incubation time, the oligonucleotide probe will be out-competed by the next matching oligonucleotide probe that is interrogating the next position, which is in much higher concentration and hence has a higher hybridization on-rate.

Other possibilities to detect hybridization than direct fluorescence are energy transfer methods (FRET), and sequential hybridization of oligonucleotide probes labeled with only one fluorophore each.

In order to discriminate the hybridization of the matching oligonucleotide probe from the mismatching other oligonucleotide probes, a variety of probe parameters, buffer compositions and temperatures can be used in order to achieve tr-SBH. The complexity of the oligonucleotide probes can be varied. It is desirable to keep the oligonucleotide probes short, preferably 5-9 nucleotides, in order to obtain optimal match-mismatch discrimination. The shorter the oligonucleotide probes the more a mismatch effects the hybridization of an oligonucleotide probe. Oligonucleotide probes can, however, be longer, up to 30 bases and the discrimination reaction can still be efficient. In order to increase the specificity with such long probes, a variety of buffer additions can be used to decrease the Tm of oligonucleotide probes which increases the match-mismatch discrimination, for example addition of formamide.

Short oligonucleotide probes can be stabilized in order for them to hybridize effectively. Stabilization can be achieved:

Through modification of the nucleotides within the oligonucleotide probe, for example, by use of LNA nucleotides, PNA nucleotides or minor groove binders.

Through the addition of degenerate positions at both sides of the oligonucleotide probe, extending the probe length without increasing the complexity. A 5-mer oligonucleotide probe can for example be extended with an N and make the oligonucleotide probe a 7-mer with the same specificity as the 5-mer but Tm of a 7-mer.

Through stabilizing additives in the hybridization reaction, for instance salt, cetrimonium bromide (CTAB), magnesium, trimellitic anhydride chloride (TMAC) and/or stabilizing proteins.

Through a combination of all above, for example, a degenerate probe with LNA hybridized in CTAB buffer.

Figure 18A:
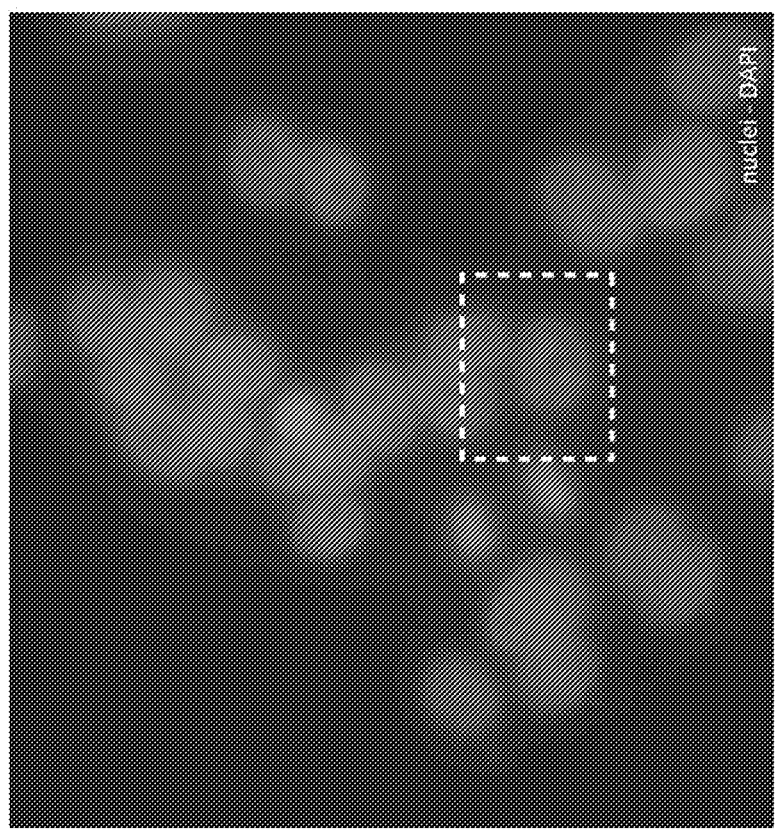
FIG. 18 illustrates the results of a tr-SBH smFISH experiment of the gene-specific barcode sequence in the general overhang sequence for the her2 gene in MCF7 cells. a) The image shows the nuclei staining and the region of interest. b) Show zoomed in versions of the region of interest. Top panel images: Individual frames (1 image) of all fluorescent channels G, T and A. Only one or two smFISH signals may be slightly visible in the A-Cy® 5 (dye) channel already with 1 frame. Bottom panel images: Average intensity projections of 25 frames for each fluorescent channel G, T and A. Several smFISH signals are distinguishable above the background after image integration only in the base A-specific Cy® 5 (dye) channel (indicated by arrows).
Figure 18B:
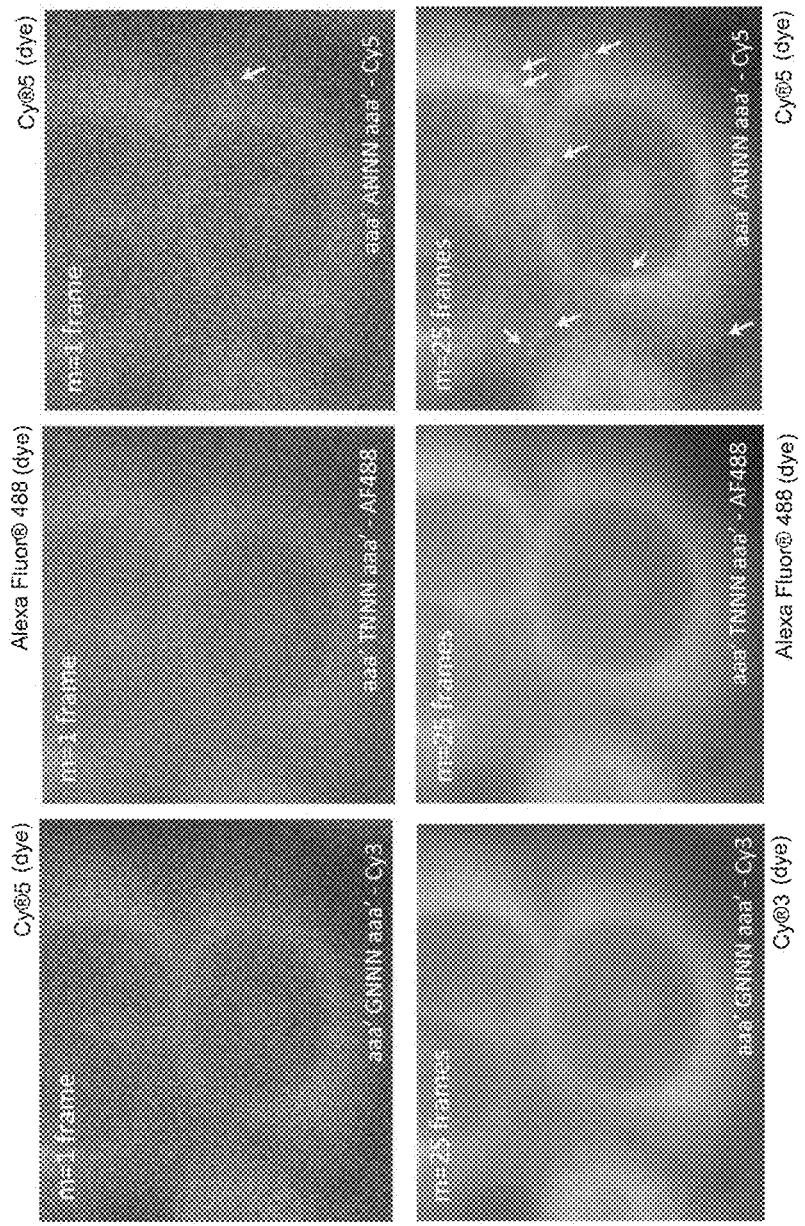

FIGS. 18A and 18B illustrate the time-resolved sequencing by hybridization of such hybridization probe overhangs in a single molecule fluorescent hybridization reaction inside preserved cells.

Figure 19A:
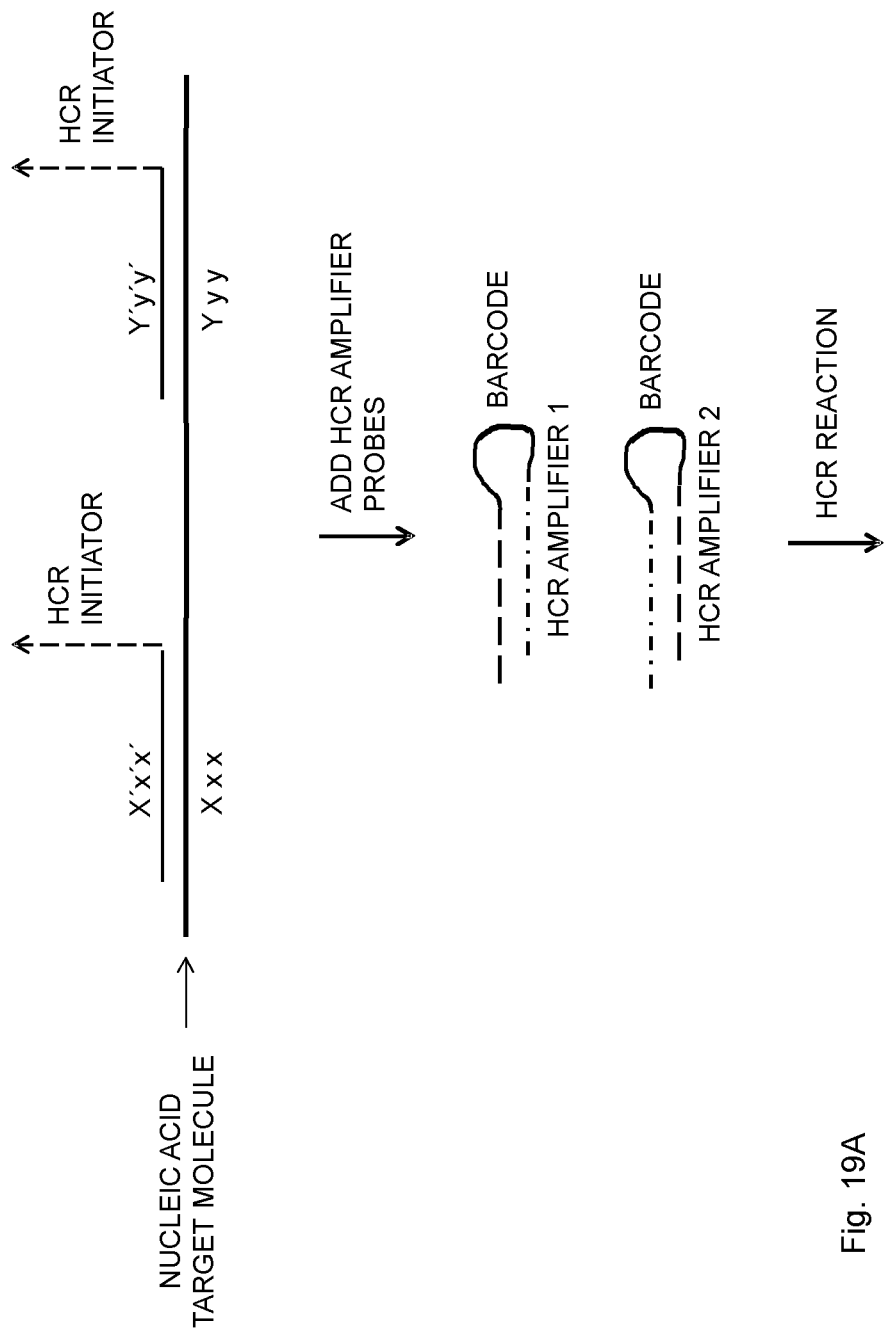
FIG. 19 illustrates NAA generated through concerted hybridization of probes on individual nucleic acid molecules. a) Hybridization probes comprise a respective complementary sequence and a non-hybridizing common overhang sequence with a sequence that is unique for the identified nucleic acid molecule, and common for all hybridization probes hybridizing to the same nucleic acid molecule. The overhang sequence can serve as initiator for hybridization chain reaction (HCR). HCR amplifier probe sets (here 2 sets are illustrated) carry gene-specific barcode sequence (here illustrated in the loop region of the HCR probes). HCR probes are added to the NAA to start the HCR. b) During the HCR reaction the overhang of the NA hybridization probes initiates the HCR by opening up the hairpin structure of the HCR probe that carries a sequence that is complementary to the initiator sequence. The hairpin unfolds when hybridizing and reveals the sequence that is complementary to one arm of the second HCR probe. During the HCR reaction the signal is amplified by accumulating many gene-specific HCR probes on the position of the detected NA. All HCR probes carry the gene-specific barcode sequence that is, after HCR reaction, single stranded and therefor accessible for a sequencing reaction. c) Sequencing oligonucleotides (here illustrated for the $2^{nd}$ base position of a 4N barcode sequence) are added to the HCR products. The sequencing reaction can be monitored over several imaging frames and the correct barcode base can be identified through time-resolved image processing as described in the previous examples. The advantage of using tr-SBH to read the barcode sequences in HCR products is that the HCR product does not need to be disassembled and re-assembled in order to sequence the next base. The sequencing mix for the next base can simply be added to the existing HCR product and the sequencing oligonucleotide from the previous base will quickly dissociate and be replaced with the sequencing oligonucleotide for the next base position.
Figure 19B:
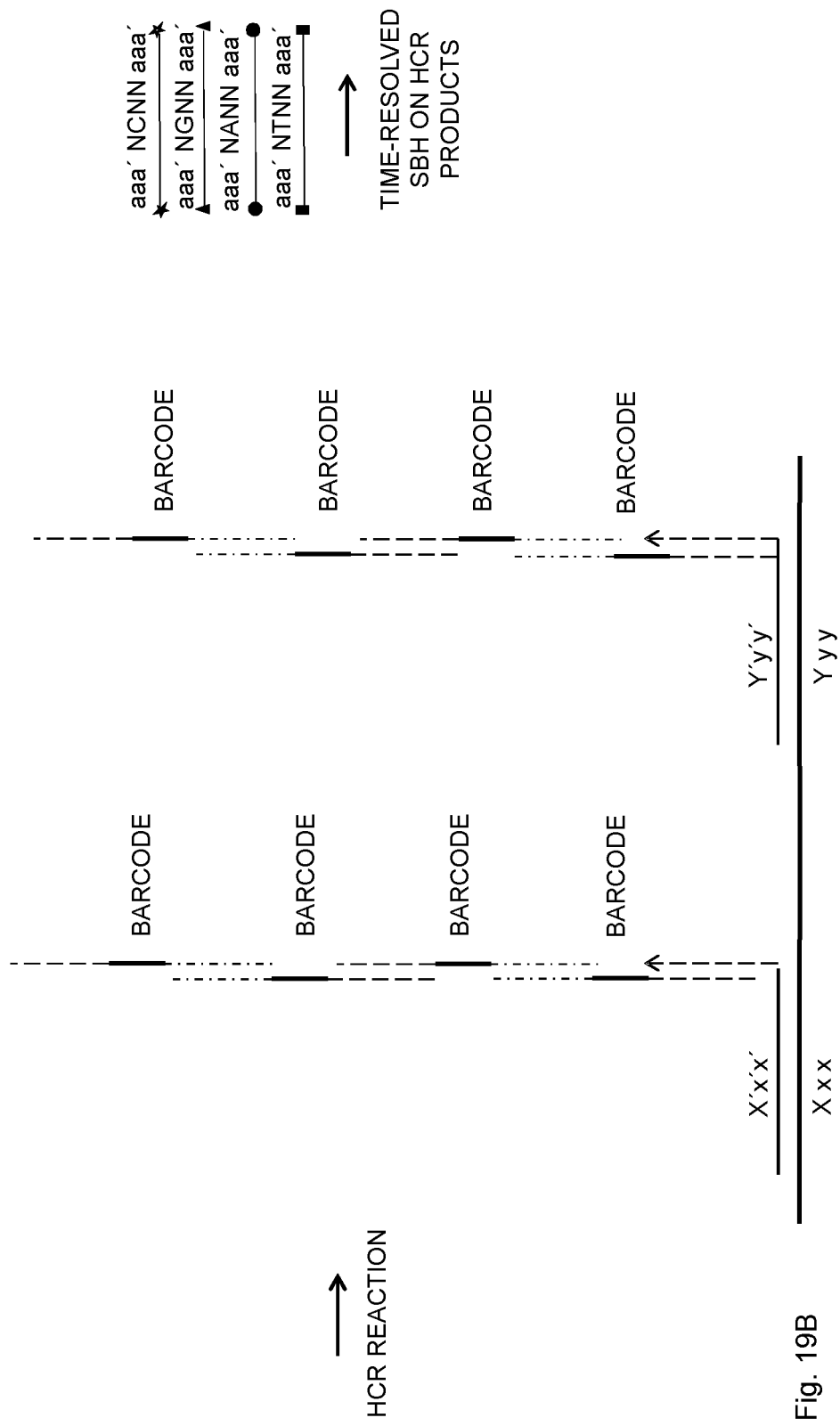
Figure 19C:
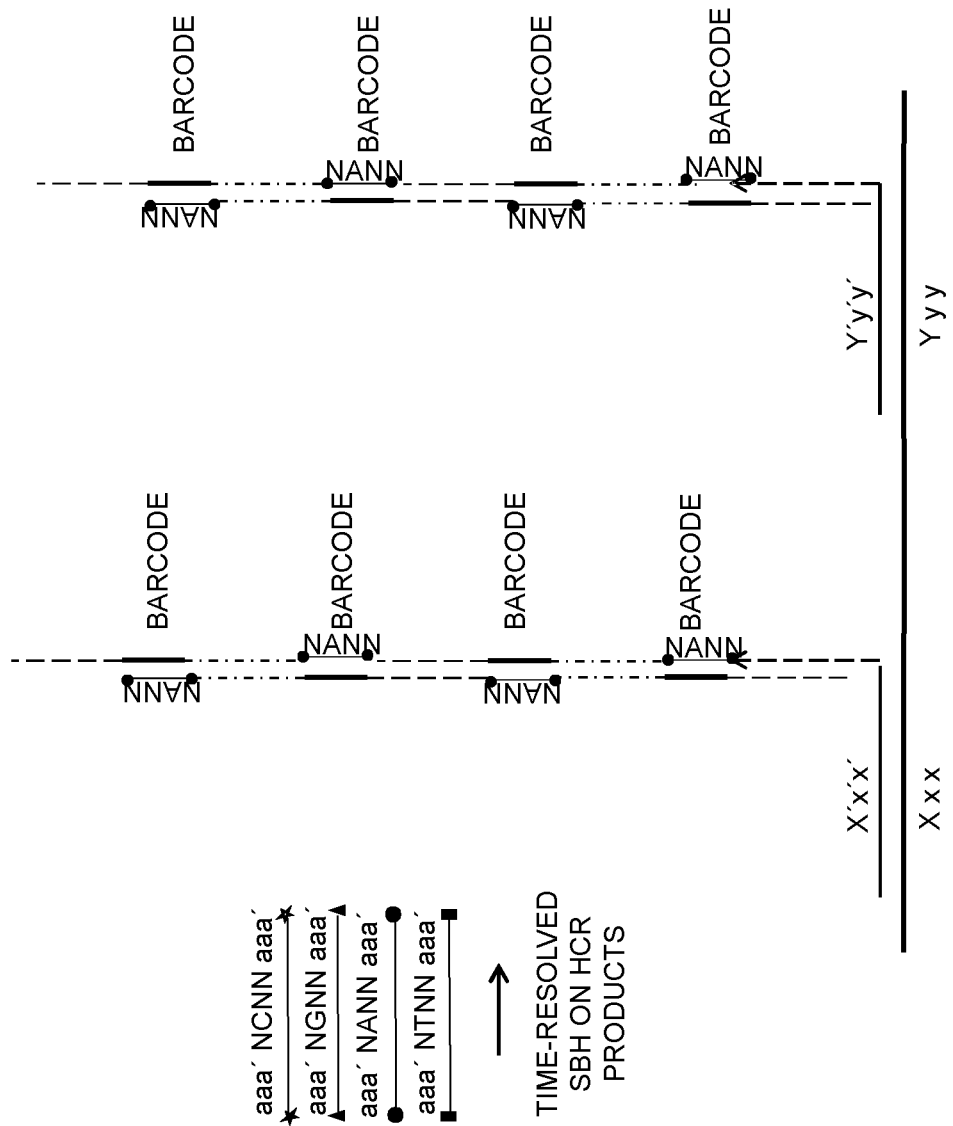

FIG. 19 illustrates NAA generated through concerted hybridization of probes on individual nucleic acid molecules. As shown in FIG. 19A, hybridization probes comprise a respective complementary sequence and a non-hybridizing common overhang sequence with a sequence that is unique for the identified nucleic acid molecule, and common for all hybridization probes hybridizing to the same nucleic acid molecule. The overhang sequence can serve as initiator for hybridization chain reaction (HCR). HCR amplifier probe sets (here 2 sets are illustrated) carry gene-specific barcode sequence (here illustrated in the loop region of the HCR probes). HCR probes are added to the NAA to start the HCR. During the HCR reaction, see FIG. 19B, the overhang of the NA hybridization probes initiates the HCR by opening up the hairpin structure of the HCR probe that carries a sequence that is complementary to the initiator sequence. The hairpin unfolds when hybridizing and reveals the sequence that is complementary to one arm of the second HCR probe. During the HCR reaction the signal is amplified by accumulating many gene-specific HCR probes on the position of the detected NA. All HCR probes carry the gene-specific barcode sequence that is, after HCR reaction, single stranded and therefor accessible for a sequencing reaction. Sequencing oligonucleotides (here illustrated for the $2^{nd}$ base position of a 4N barcode sequence) are added to the HCR products as shown in FIG. 19C. The sequencing reaction can be monitored over several imaging frames and the correct barcode base can be identified through time-resolved image processing as described in the previous examples. The advantage of using tr-SBH to read the barcode sequences in HCR products is that the HCR product does not need to be disassembled and re-assembled in order to sequence the next base. The sequencing mix for the next base can simply be added to the existing HCR product and the sequencing oligonucleotide from the previous base will quickly dissociate and be replaced with the sequencing oligonucleotide for the next base position.

Accordingly, step S2 of FIG. 1 comprises performing the (light) measurements, at least at the spatially defined site, at the M time instances during i) a hybridization reaction or ii) a ligation reaction comprising i) hybridization of the N oligonucleotide probes to the target nucleic acid sequence or ii) ligation of the N oligonucleotide probes to an anchor probe complementary to a segment of a nucleic acid molecule comprising the target nucleic acid sequence to form the M data sets.

This means that the i) tr-SBH or ii) tr-SBL of the embodiments can be performed during the actual i) hybridization or ii) ligation reaction. There is, therefore, no need to await the long incubation time and perform any washing prior to measurements as in the prior art SBH and SBL reactions that are based on end-point measurements.

The oligonucleotide probes of the embodiments can comprise naturally occurring nucleotides and thereby be in the form of a DNA or RNA oligonucleotide probe. The oligonucleotide probes may, alternatively, comprise nucleic acid analogous and/or artificial or synthetic nucleotides, such as PNA, LNA, GNA and/or TNA. In such a case, the oligonucleotide probes may solely comprise such nucleic acid analogous and/or artificial or synthetic nucleotides or a mixture of naturally occurring nucleotides and nucleic acid analogous and/or artificial or synthetic nucleotides.

The oligonucleotides probes preferably have a length of from 4 nucleotides up to 50 nucleotides. Preferably, the oligonucleotide probes have a length of at least 5, 6 or 7 nucleotides. The oligonucleotide probes preferably have a length of no more than 40, 35, 30, 25, 20 or 15 nucleotides. The oligonucleotide probes preferably have a length of 5 to 15 nucleotides, more preferably 5 to 12 nucleotides and even more preferably 5 to 9 or 8 to 10 nucleotides.

Oligonucleotide probes having a label, such as a fluorescent label, could comprise the label at the 5' end, at the 3' end, or a first label at the 5' end and a second label, which may be the of the same type or different type as first label, at the 3' end.

FIG. 6 is a flow chart illustrating additional, optional steps of the method shown in FIG. 1. The method continues from step S2, S3 or S4 in FIG. 1. A next step S40 comprises removing the N oligonucleotide probes. Thereafter steps S1 to S3 or S1 to S2 are repeated but with N new oligonucleotide probes. The method then continues to step S41, which comprises determining a next sequenced base of the target nucleic acid sequence based on the identified label or the identified absence of any label.

FIG. 6 thereby illustrates the additional method steps for sequencing a next base position or a next set of base positions in the target nucleic acid sequence. Firstly, the N oligonucleotide probes used in the previous cycle are removed typically by simply pipetting, pouring, flowing or otherwise removing the N oligonucleotide probes or the reaction mixture from the spatially defined site. Then a new reaction mixture with the N new oligonucleotide probes is added in the new round of step S1. A new set of (light) measurements is performed in the new round of step S2 to obtain M new data sets.

In an embodiment, the cycle of step S40 and steps S1 and S2 is repeated until all base positions, or at least a portion thereof, in the target nucleic acid sequence are interrogated, which is schematically illustrated by the loop L1 in FIG. 6. This approach generates M data set for each cycle of the loop L1. Once all base positions have been interrogated, the method can continue to step S3, which co-processes, for each cycle of the loop L1, the respective M data sets in order to identify a label or absence of any label at the spatially defined site. This co-processing can be performed serially for each cycle and base position or at least partly in parallel. The respective sequenced base positions are then determined in step S41.

In another embodiment, the cycle of step S40, steps S1-S3 and step S41 is repeated until all base positions in the target nucleic acid sequence are sequenced, which is schematically illustrated by the loop L2 in FIG. 6. In this embodiment, each base position is interrogated and sequenced prior to continuing to the next base position in the target nucleic acid sequence.

Thus, it is evident from the disclosure above that the method steps S1 and S2 are performed serially but the co-processing step S3 and the determining step S4 can be performed at least partly in parallel and either directly following steps S1 and S2 or at a point later in time, such as after performing steps S1 and S2 for each base position in the target nucleic acid sequence to be determined.

In a particular embodiment, the N new oligonucleotide probes used in second and further cycles of the loop L1 or L2 preferably have a higher affinity to the target nucleic acid sequence as compared to the N oligonucleotide probes.

Hence, it may be preferred that the N oligonucleotide probes used in one cycle of the loop L1 or L2 have higher affinity to the target nucleic acid sequence as compared to the N oligonucleotide probes used in the previous cycle(s). In such a case, the N new oligonucleotide probes will more efficiently out-compete the oligonucleotide probes used for sequencing previous base positions.

Increasing affinity can be achieved according to various embodiments. In a first approach, the affinity is increased by increasing the length of the oligonucleotide probes. For instance, in the first cycle oligonucleotide probes of a length L are used, whereas in the second cycle the length of the new oligonucleotide probes is L+h, wherein h is a positive integer equal to or larger than one. For instance, the oligonucleotide probe length can increase by one nucleotide for each cycle and base position to interrogate.

Tr-SBH can be used in combination with any probe displacement and sequential hybridization strategies, such as for example toehold probes. These probing strategies may help removing oligonucleotide probes from the sequencing reaction of one nucleotide position with the oligonucleotide probe that interrogates the next nucleotide position.

Alternatively, or in addition, one could start by using oligonucleotide probes in the first cycle that have one or more mismatches in the sequence part that is constant for all oligonucleotide probes and does not contain the target nucleic acid sequence, and merely exhibits a stabilizing (Tm increasing) function, such as sequencing library oligonucleotide probes drawn in FIG. 8. In the next sequencing cycle the next oligonucleotide probe that is added to sequence the second base may carry one less mismatch than the previous oligonucleotide probe and, hence, has more affinity.

Alternatively, or in addition, non-naturally occurring nucleotides having higher affinity as compared to the naturally occurring nucleotides could be used. For instance, the number of LNA nucleotides could increase in each cycle, such as 0 LNA nucleotides for the first cycle, 1 LNA per oligonucleotide probe for the second cycle and so on.

It is of course possible to combine usage of "sticky" nucleotides with increasing probe lengths in order to increase the affinity of oligonucleotide probes to the target nucleic acid sequence.

The nucleic acid sequencing method of the embodiments can advantageously be used to sequence so-called nucleic acid accumulations (NAAs). NAA implies that a target nucleic acid sequence is present in high concentration or high copy number at the spatially defined site. Such NAA may originate from, for instance, localized DNA amplification mechanisms or from the hybridization of several single-stranded hybridization probes to proximal locations on the same nucleic acid molecule (see FIG. 10). Non-limiting examples of DNA amplification methods include polymerase chain reaction (PCA), helicase-dependent amplification (HDA), loop mediated isothermal amplification (LAMP), multiple strand displacement amplification (MDA) or rolling circle amplification (RCA).

NAAs can also be generated by proximity ligation assay (PLA) and RCA of the PLA reporter molecule, which is also applicable in situ inside preserved cells and tissues. NAAs can also be generated by immuno-RCA, in which protein binders, such as antibodies, carry a protein-specific oligonucleotide sequence that can be sequenced or first amplified through for example RCA and then sequenced.

NAAs can further be generated by hybridization of hybridization probes to RNA and DNA molecules, which serve as a guiding template or scaffold for the spatial accumulation of these hybridization probes into a distinct spatial position defined by the location of the RNA or DNA molecule, as described in [2]. The herein described method can be used to sequence barcodes that can be placed into non-hybridizing overhang sequences within these individual hybridization probes as shown in FIG. 10, where the hybridization probes comprise following features:

- A hybridization sequence that hybridizes to a segment within a nucleic acid molecule that is unique for only this nucleic acid species. Different hybridization probes are designed to hybridize at different segments within the same nucleic acid molecule, in certain distance from one another.
- A common overhang sequence with a common barcode sequence that identifies the detected nucleic acid molecule.
- Optionally, the hybridization probes can contain a common label, such as a fluorophore, which identifies NAAs in general.
- Optionally, the hybridization probes can contain a cross-linking agent for crosslinking the hybridization probes to proteins, or to a gel matrix.
- Optionally, the overhang sequence can serve as template for the hybridization of more hybridization probe sequences for a NAA increase, which can increase the sequencing signal density.
- Alternatively, additional hybridization probes can be hybridized to the non-hybridizing overhang sequence of the initial segment-binding hybridization probes, which themselves can serve as template for the hybridization of even more hybridization probes, such as in branched DNA technology and in hybridization chain reaction (HCR). These two mechanisms can also be used to generate NAAs that can be sequenced with the herein described method.

Figure 11:
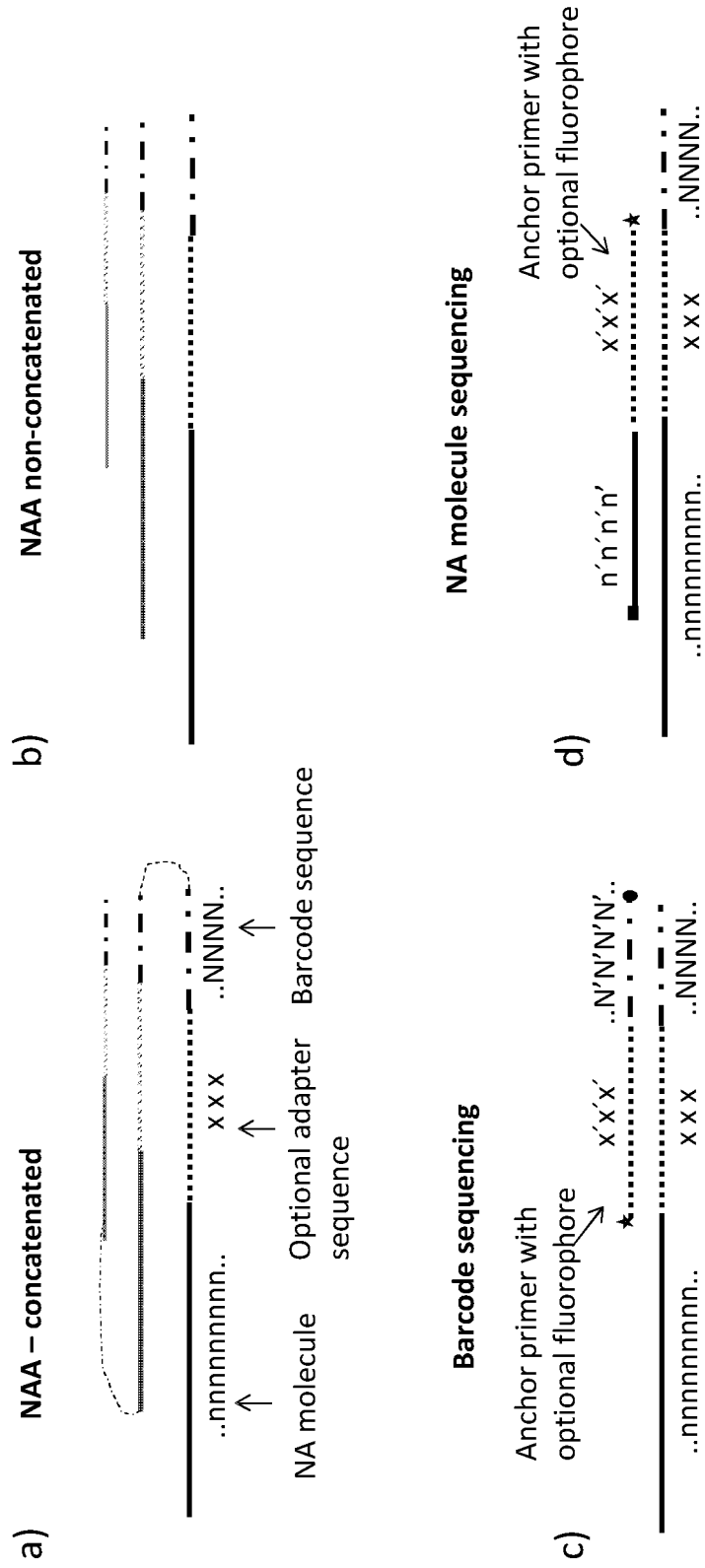
FIG. 11 illustrates a general concept of NAA sequencing of a) concatenated NAAs or b) non-concatenated NAAs. c) Sequencing barcode motifs introduced into the NAA, or d) sequencing of the nucleic acid molecule (NAA).

The common denominator for NAAs that can be sequenced with tr-SBH and tr-SBL is a spatially defined accumulation of nucleic acids is generated at a given spatial position that can be used as sequencing substrates. Within NAA either barcode sequences can be sequenced or the sequence of the target molecule sequence itself can be sequenced, see FIGS. 11C and 11D. FIG. 11 also illustrates examples of generating concatenated (FIG. 11A) and non-concatenated (FIG. 11B) NAAs.

NAAs can be generated from different sample types and in different environments, i.e., NAAs can be generated on a planar surface, inside polymer gels, on beads or in situ inside cells or tissues. To sequence NAAs with tr-SBH and tr-SBL in tissues, the tissues may first be embedded into gel matrices and the NAAs may be crosslinked onto the matrix of such a gel with preserving the spatial positioning within the specimen. Biological material may then be removed from the gel, while the NAAs stay left behind in their spatially defined position, after which they may be sequenced by tr-SBH and tr-SBL.

The present embodiments enable faster and more accurate sequencing of spatially defined and fixated target nucleic acid sequences or NAAs through time-resolved light, such as fluorescent, measurements. Instead of measuring the end point of a sequencing reaction, after removal of reaction mixture and washing, the proposed method measures the sequencing reaction at several time points during the ongoing reaction, without the need to remove the reaction mixture and washing. In fact, this method takes advantage of the presence of large excess of (fluorescently) labeled oligonucleotide probes by exploiting the competition between the oligonucleotide probes. As such, the correct oligonucleotide probes with the complementary sequence occupies the sequenced interrogation site to a larger extent than competing oligonucleotide probes that are not fully complementary to the target nucleic acid sequence due to a smaller hybridization binding constant than fully complementary oligonucleotide probes. A single light, such as fluorescent, measurement does not resolve the transient binding of the correct oligonucleotide probe, because the concentration of fully matching correct oligonucleotide probe occupying the target nucleic acid sequence within a NAA at one time point t is not significantly higher than the concentration of mismatching incorrect oligonucleotide probes occupying the same NAA position at time point t by i) hybridization to the NAA despites mismatch or ii) occupation of the same voxel without actually hybridizing to the target nucleic acid sequence. Moreover, diffusion and random Brownian motion of oligonucleotide probes leads to a considerable fluorescent noise in the same voxel position of a NAA, so that a NAA, despites its local increase of correct matching oligonucleotide probes compared to its surrounding, is not visible above the fluctuating noise in one measurement.

Through time resolved measurement the correct signal can be distinguished from the fluctuating noise. By measuring the ongoing reaction several times during the reaction and integrating the measurements the true sequencing signal can already be identified during the reaction, see FIG. 13. This can be done by mathematical image integration through plotting pixel or voxel values with the lowest (minimum intensity projection) or highest (maximum intensity projection) pixel values within all individual frames or images into one image, or by averaging or summing up all intensities within one pixel or voxel from the obtained images or frames, see FIG. 14C. As a result, the less fluctuating fluorescent intensity of the correct oligonucleotide probe occupying the NAA, compared to the fluorescent intensity of the other oligonucleotide probes, coding for other bases, that are strongly fluctuating throughout the different images, can be used to identify the sequenced base out of the background, see FIGS. 13 and 14A.

In a particular embodiment, the sequenced base inside a NAA is identified by measuring the fluorescent intensity in all fluorescent channels inside the NAA and outside the NAA, see FIG. 7, and forming the ratio of intensityNAA/intensityBackground. With increasing number of images or frames that are integrated the signal-to-noise ratio (SNR) significantly increases and the sequenced base can be identified based on the significantly higher SNR within the NAA compared to the other fluorescent colors coding for the other bases, see FIGS. 13 and 14B.

The embodiments can be used to improve SBH and SBL reactions, in regard to both reaction speed and accuracy.

Advantages of tr-SBH of NAAs, generated in situ inside persevered tissues, and especially in thick gel-embedded and cleared tissue specimens, through single molecule fluorescent in situ hybridization (smFISH), are that the short oligonucleotide probes rapidly diffuse into the thick specimens so that the tr-SBH reaction can be imaged in relative short time after the reaction mixture is applied. The fast diffusion into and out of the specimen is then a big advantage when using tr-SBH in order to record the dissociation of oligonucleotide probes from one base position and the association of oligonucleotide probes for the next base position in many NAAs simultaneously, making the sequencing process very fast and more accurate than when using end point measurements.

The embodiments increase both speed and accuracy of base calling during sequencing by measuring, for instance, fluorescence during incorporation and dissociation of oligonucleotide probes at multiple time points during the sequencing reaction. The observed differences can be used to a) identify NAAs, b) identify the sequenced base on the interrogated position, c) measure kinetics of association and dissociation of oligonucleotide probes in individual NAAs.

The time-resolved measurements of the embodiments can also be used to measure kinetics of hybridization and melting of oligonucleotide probes onto the target nucleic acid sequence. The information about the kinetics can be interesting in itself from a fundamental perspective but may also be useful to determine a base or barcode position. For example, it could be used to measure if an oligonucleotide probe matches perfectly or whether it has a mismatch. If it has a mismatch it may be replaced faster than an oligonucleotide probe that has no mismatch.

The present embodiments improve any technology that relies on hybridization of oligonucleotide probes to NAAs for detection and identification of these NAAs. This includes any sequencing-by-ligation, sequencing-by-hybridization, in situ hybridization technique.

Applications of the embodiments include sequencing of individual DNA and RNA molecules from solutions and DNA and RNA molecules in situ inside cells and tissue sections of different thickness and origin. Any sequencing method that relies on SBH and SBL on spatially defined NAAs can benefit from the present embodiments, by increasing sequencing reaction speed and accuracy.

One field of application is sequencing NAAs directly in situ in tissue for multiplexed gene expression quantification, splice variant detection and point mutation analysis, i.e., in situ sequencing. Applications lie both in fundamental research and in diagnostics where the spatial context adds crucial information. Areas include neuroscience and cancer research. Cancer research and diagnostics vastly benefit from in situ sequencing methods by supplying spatial information about mutations and gene expression aberrations which enables to study cancer heterogeneity. A deeper understanding of the heterogeneity of a cancer in turn helps defining which drugs should be used to achieve best outcome of patient treatments.

Applications that require spatial localization of biomarkers are traditionally addressed by immunohistochemistry and in situ hybridization. Unlike in situ sequencing, these techniques are severely limited in the number of biomarkers that can be distinguished in parallel.

EXAMPLES

Example 1: Gene Expression Profiling by Time Resolved Sequencing by Ligation (tr-SBL) of Nucleic Acid Accumulations (NAAs) Immobilized on a Planar Glass Surface Generation of NAAs for Time Resolved Sequencing (Library Preparation)

NAAs were generated through rolling circle amplification (RCA) in homogeneous solution. Circular templates for RCA, containing a sequencing barcode, were generated by ligation of circular probes in a ligation mixture composed of: 10 nM circular probe, 30 nM ligation template, T4 ligase reaction buffer 1× (66 mM Tris-HCl (pH-7.5), 10 mM dithiothreitol (DTT), 10 mM $MgCl_2$, DNA-Gdansk), bovine serum albumin (BSA) 0.2 µg/µL and 1 U T4 ligase (DNA-Gdansk) in 100 µL reaction volume, incubated at 37° C. for 20 minutes. The reaction was heat inactivated at 65° C. for 2 min. Ligated circles were diluted to 100 pM concentration and amplified by rolling circle amplification in a reaction mixture composed of 100 pM ligated circles, BSA 0.2 mg/mL, phi29 polymerase reaction buffer 1× (33 mM Tris-acetate (pH-7.9), 10 mM Mg-acetate, 66 mM K-acetate, 0.1% (v/v) Tween® 20 (nonionic detergent), 1 mM DTT, Thermo Scientific), 125 µM dNTPs (DNA Gdansk) and 0.2 U/µL phi29 polymerase (O-Link, Sweden), incubated at 37° C. for 60 minutes.

RCA products (RCPs) were applied onto poly-L-lysine coated #1.5 (1.7 mm thickness) cover slip (ThermoFisher) and incubated for 5 min to bind RCPs to the surface. The solution was then removed and the cover slip was washed once in phosphate-buffered saline (PBS)-0.05% Tween® (nonionic detergent).

A flow cell was then attached to the cover slip.

tr-SBL of NAAs on the Glass Surface

A hybridization mixture containing 100 nM of corresponding anchor probes, labelled with Alexa750 (Alexa Fluor® 750 (dye)) in 2× saline sodium citrate (SSC) and 20% formamide was added through the flow cell. The hybridization mixture was removed followed by a PBS wash. The sample with attached flow cell was then mounted in a microscope (Zeiss Axio Imager Z.2) fitted with a sCMOS camera (Hamamatsu ORCA-Flash 4.0) and a 20× high-numerical aperture objective (Zeiss Plan-Apochromat 20×/0.8) to monitor the sequencing reaction over time. The imaging system was focused on the anchor probe stain of the RCPs. Then, a ligation mixture containing each oligonucleotide probe (100 nM each), 1× T4 ligase buffer (DNAGdansk), 1 mM ATP (Fermentas) and 0.1 U/µl of T4 ligase (DNAGdansk) was applied through the flow cell and imaged over time.

Image Processing and Base Calling for tr-SBL Reaction

Single image frames of anchor probe and oligonucleotide probe specific channels were recorded at multiple time points (100 ms exposures, 15 time points). Recorded raw data of individual frames of anchor probe and oligonucleotide probes were exported as tagged image file format (TIFF) files. Average intensity projections were calculated from the anchor probe image series after washing. The CellProfiler software [1] was used to process projection images. In particular, the projection images were high-pass (top-hat) filtered to emphasize RCP-sized details and to suppress lower frequencies corresponding to larger details, such as nuclei and cell body. The resulting size-filtered images were segmented into RCP areas 1 and surrounding local background 2, based on an empirically determined manual intensity threshold, see FIG. 7. Intensity values $I_1$ and $I_2$ were extracted from both compartments 1, 2 see FIG. 7 by calculating the average intensity values in respective area 1, 2. The ratios between RCP intensity ($I_1$) and intensity of local background ($I_2$) were calculated for individual amplicons at multiple time points.

Figure 12:
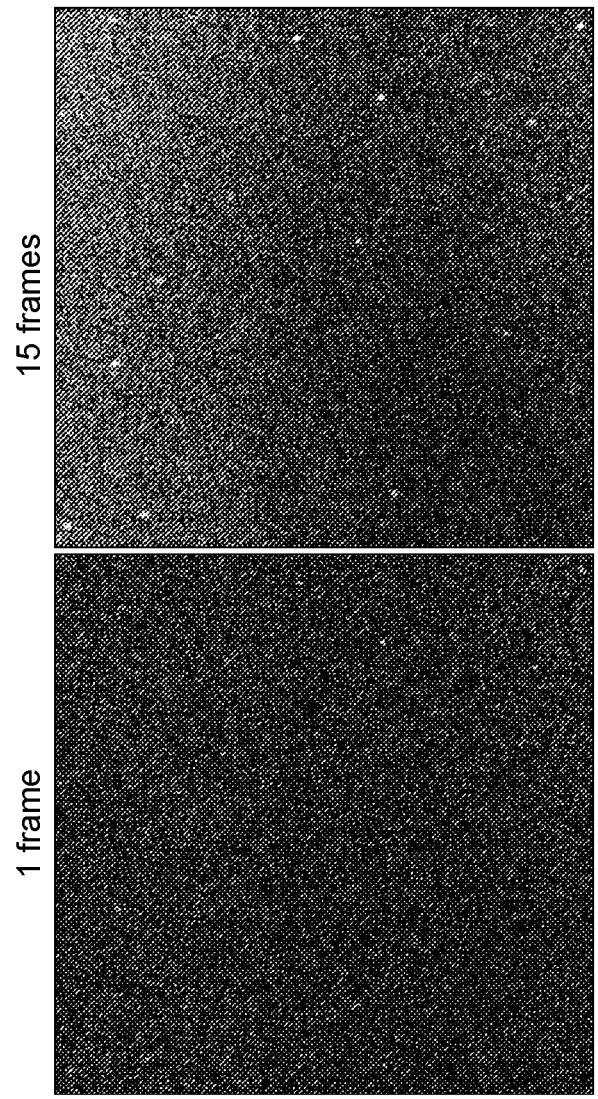
FIG. 12 illustrates an RCP labeling reaction. RCPs are barely visible in presence of ligation mixture with free oligonucleotide probes (1 frame). When multiple frames (15 frames) are combined in an average intensity projection, RCPs are visible as white speckles since background is reduced due to higher fluctuation of fluorophore-conjugated oligonucleotide probes in background as compared to RCPs, onto which oligonucleotide probes hybridize.

FIG. 12 illustrates an RCP labeling reaction. RCPs are barely visible in presence of ligation mixture with free oligonucleotide probes (1 frame). When multiple frames (15 frames) are combined in an average intensity projection, RCPs are visible as white speckles since background is reduced due to higher fluctuation of fluorophore-conjugated oligonucleotide probes in background as compared to RCPs, onto which oligonucleotide probes hybridize.

FIG. 13 illustrates the results of the tr-SBL experiment. The diagram illustrates signal-to-noise ratio of average pixel intensity inside a defined RCP and averaged background around one RCP. The X axis represents arbitrary time units (time point 5 is 3.20 min). The anchor primer stains a RCP prior to the real time measurement, to which the sequencing library (A, C or T) is ligated. The sequencing library to interrogate guanine (G) has not been plotted since its fluorophore is used by the anchor primer. True complementary signal is base C. The base C can be called already from time point 6 or 7.

Example 2: Time Resolved Sequencing by Hybridization (tr-SBH) of Nucleic Acid Accumulations (NAAs) Immobilized on a Planar Glass Surface Generation of NAAs for Time Resolved Sequencing (Library Preparation)

NAAs were generated through rolling circle amplification (RCA) in homogeneous solution. Circular templates for RCA, containing a sequencing barcode, were generated by ligation of circular probes in a ligation mixture composed of: 10 nM circular probe, 30 nM ligation template, T4 ligase reaction buffer 1× (66 mM Tris-HCl (pH-7.5), 10 mM dithiothreitol (DTT), 10 mM MgCl$_2$, DNA-Gdansk), bovine serum albumin (BSA) 0.2 µg/µL and 1 U T4 ligase (DNA-Gdansk) in 100 µL reaction volume, incubated at 37° C. for 20 minutes. The reaction was heat inactivated at 65° C. for 2 min. Ligated circles were diluted to 100 pM concentration and amplified by rolling circle amplification in a reaction mixture composed of 100 pM ligated circles, BSA 0.2 mg/mL, phi29 polymerase reaction buffer 1× (33 mM Tris-acetate (pH-7.9), 10 mM Mg-acetate, 66 mM K-acetate, 0.1% (v/v) Tween® 20 (nonionic detergent), 1 mM DTT, Thermo Scientific), 125 µM dNTPs (DNA Gdansk) and 0.2 U/µL phi29 polymerase (O-Link, Sweden), incubated at 37° C. for 60 minutes.

RCA products (RCPs) were applied onto Superfrost™ microscope glass slides (ThermoFisher) and incubated for 15 min to bind RCPs to the surface. The solution was then removed and the glass slide was washed once in phosphate-buffered saline (PBS)-0.05% Tween® (nonionic detergent). Sequencing Barcodes in RCA Products Immobilized on a Glass Surface Using Time-Resolved Sequencing by Hybridization (tr-SBH)

Figure 16A:
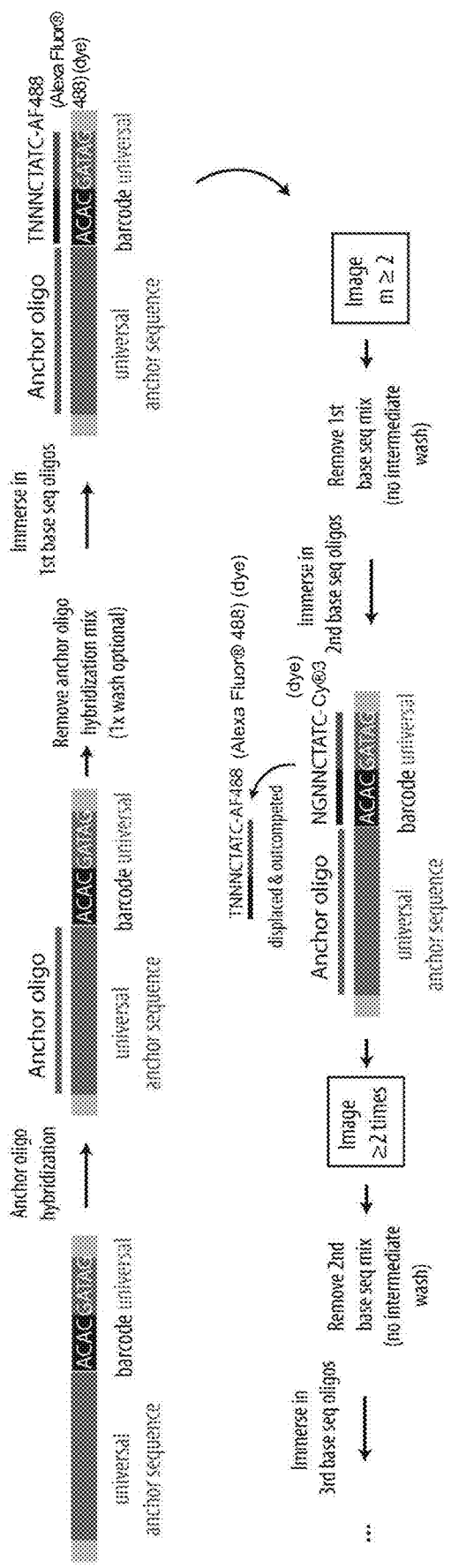
FIG. 16 illustrates the results of a tr-SBH experiment of the $1^{st}$, $2^{nd}$ and $3^{rd}$ base of the barcode sequence ACAC in RCA products. a) Detailed illustration of the procedure. b) Sequencing oligonucleotides used in the $1^{st}$, $2^{nd}$ and $3^{rd}$ base sequencing reaction. c) Summed images of 7 time individual points, with arbitrary intermediate time, allow for discrimination of signal from background. Signal to noise ratios (S/N) are calculated as described in connection with FIG. 7, and plotted next to the segmented objects in the images. Summed pixel intensity in RCP defining area/minimum intensity in local background of individual RCPs at 7 time points. First columns of images show time-integrated images from sequencing base 1, second column from base 2 and $3^{rd}$ column from base 3. The corresponding base call, i.e., the highest S/N ratio in each object, is plotted in the last image of each column, which comprises the general RCP anchor probe staining. d) The barcode sequence of the first 3 bases is constructed from the 3 sequencing reactions in c).

A hybridization mixture containing 100 nM of corresponding anchor probes, labelled with Alexa750 (Alexa Fluor® 750 (dye)) in 2× saline sodium citrate (SSC) and 20% formamide was added to the glass slide and incubated at room temperature for 30 min. The hybridization mixture was removed followed by a PBS wash. Then, 20 µL sequencing mixture for the first base, containing each oligonucleotide probe (20 nM each), was applied to the immobilized RCPs in 2×SSC buffer. A cover slip was added to spread out the reaction mixture. The slide was immediately inserted into the microscope (Zeiss Axio Imager Z.2) fitted with a sCMOS camera (Hamamatsu ORCA-Flash 4.0) and a 20× high-numerical aperture objective (Zeiss Plan-Apochromat 20×/0.8) and imaging was started directly. First, the imaging system was focused on the anchor probe stain of the RCPs. Then the SBH reaction for the first base was monitored by imaging over various time points. Continuous image series were recorded for each channel (50 ms exposures, 7 frames) at multiple time points. Images were stored as raw data and exported as TIFF files for image processing. After images were acquired, the cover slip was removed, the sequencing mixture for the first base removed, and the sequencing mixture for the second base was immediately applied without prior washing as illustrated in FIG. 16A. A fresh cover slip was added to spread out the mixture. Then, the SBH reaction for the second base was monitored on the same position, exactly as for the first base. After images were acquired for the second base the sequencing mix was again removed and the sequencing mix for the $3^{rd}$ base was immediately applied and covered with a cover slip, without a prior washing step. Imaging was performed as described for first and $2^{nd}$ base.

Sequencing NA Molecule Sequences in RCA Products Immobilized on a Glass Surface Using Time-Resolved Sequencing by Hybridization (tr-SBH)

RCPs were generated and immobilized as described above in the same example. RCPs were then hybridized with the general anchor probe (AF750 (Alexa Fluor®750 (dye)) labelled) as described above. Then, after a brief PBS-Tween® (nonionic detergent) wash, 20 µL sequencing mixture for the first base, containing each NA molecule sequencing oligonucleotide probe (20 nM each), was applied to the immobilized RCPs in 2×SSC buffer. A cover slip was added to spread out the reaction mixture. The slide was inserted into the microscope. First, the imaging system was focused on the anchor probe stain of the RCPs. Then the SBH reaction for the first base was monitored by imaging over various time points. Continuous image series were recorded for each channel (50 ms exposures, 20 frames) at multiple time points. Images were stored as raw data and exported as TIFF files for image processing.

Image Processing and Base Calling for tr-SBH Reaction

Single image frames of anchor probe and oligonucleotide probe specific channels were recorded at multiple time points (50 ms exposures, various time points). Recorded raw data of individual frames of anchor probe and oligonucleotide probes were exported as tagged image file format (TIFF) files. Summed intensity projections were calculated from the anchor probe image series after washing. The resulting projection images were segmented into RCP areas 1 and surrounding local background 2, based on an empirically determined manual intensity threshold, see FIG. 7. Intensity values $I_1$ and $I_2$ were extracted from both compartments 1, 2 see FIG. 7 by calculating the average intensity values in respective area 1, 2. The ratios between RCP intensity ($I_1$) and intensity of local background ($I_2$) were calculated for all 4 channels in all individual objects, and the base in the channel with the highest S/N ratio was called.

Figures 16C, 16D:
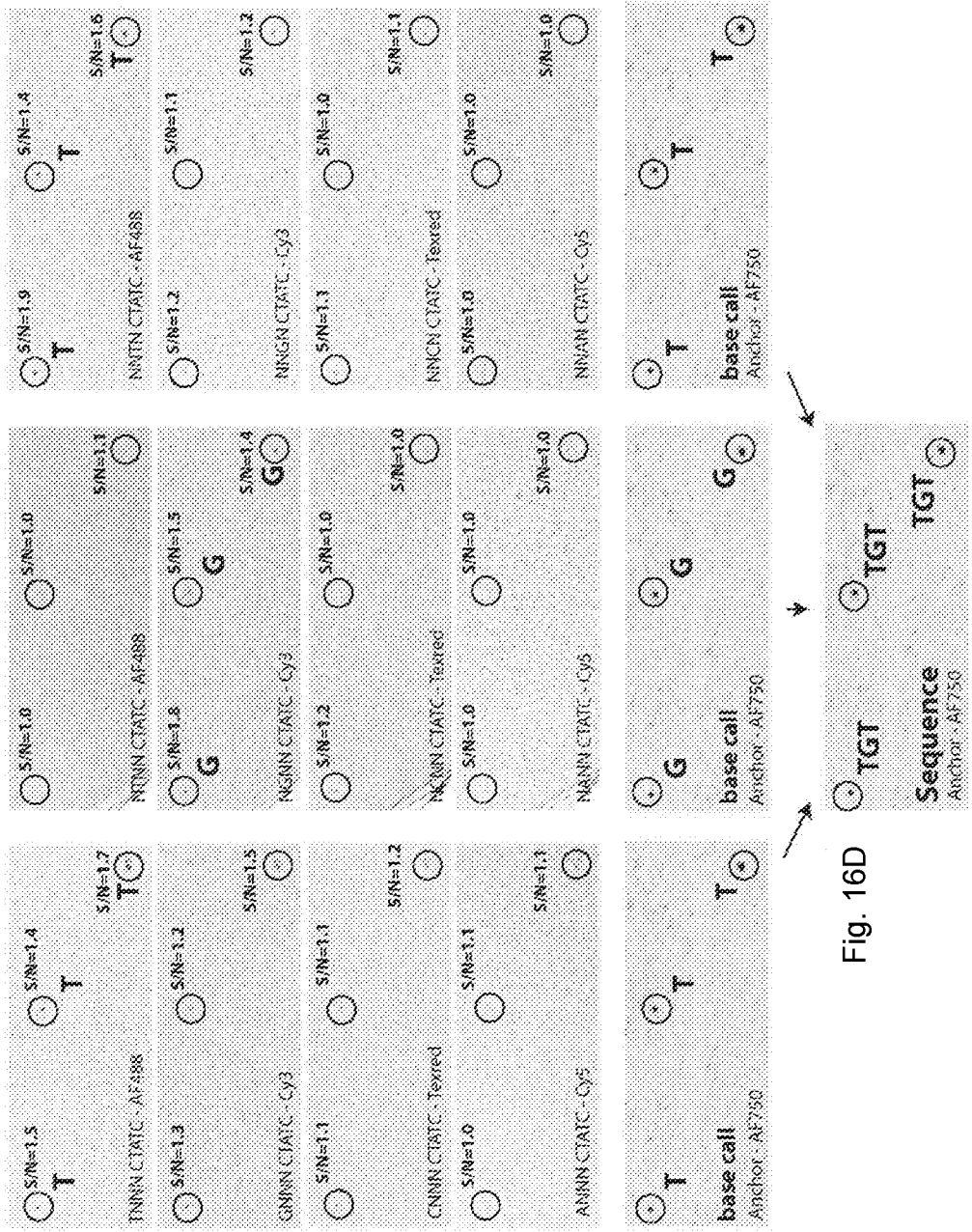

FIG. 16 illustrates the results of the tr-SBH experiment of the $1^{st}$, $2^{nd}$ and $3^{rd}$ base of the barcode sequence ACAC in RCA products. FIG. 16A is a detailed illustration of the procedure. FIG. 16B illustrates the sequencing oligonucleotides used in the $1^{st}$, $2^{nd}$ and $3^{rd}$ base sequencing reaction. FIG. 16C are summed images of 7 time individual points, with arbitrary intermediate time, allow for discrimination of signal from background. Signal to noise ratios (S/N) are calculated as described above and in FIG. 7, and plotted next to the segmented objects in the images. Summed pixel intensity in RCP defining area/minimum intensity in local background of individual RCPs at 7 time points. First columns of images show time-integrated images from sequencing base 1, second column from base 2 and $3^{rd}$ column from base 3. The corresponding base call (=the highest S/N ratio in each object) is plotted in the last image of each column, which comprises the general RCP anchor probe staining. FIG. 16D illustrates the barcode sequence of the first 3 bases is constructed from the 3 sequencing reactions in FIG. 16C.

Figure 17:
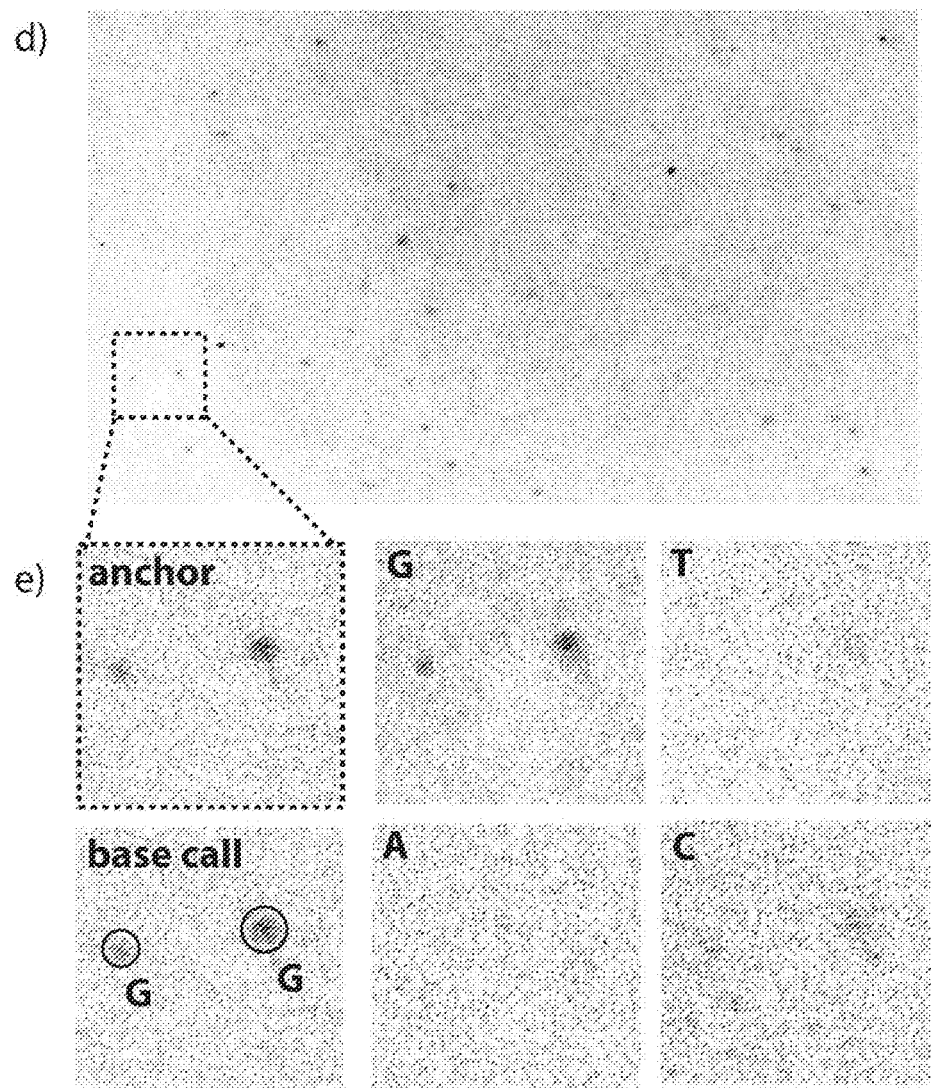
FIG. 17 illustrates the results of a tr-SBH experiment of the $1^{st}$ base of a NA molecule sequence in RCA products. a) Sequencing oligonucleotides used for the $1^{st}$ base sequencing reaction. b) Illustration of the SBH sequencing reaction. c) The actual NA sequences of the target NA and the anchor and sequencing probe. d) Anchor probe staining of RCPs immobilized on the glass surface. e) Left column: top image: zoom in area from the anchor stain in d). Bottom image: base call plotted on top of the anchor stain. Right columns: Summed images of 20 individual time points with arbitrary intermediate interval for all 4 fluorescent channels, corresponding to the base-specific staining: G, C. T and A. Base calling was based on the channel with the highest S/N ratio, as already described above.

FIG. 17 illustrates the results of the tr-SBH experiment of the $1^{st}$ base of a NA molecule sequence in RCA products. FIG. 17A illustrates the sequencing oligonucleotides used for the $1^{st}$ base sequencing reaction. FIG. 17B is an illustration of the SBH sequencing reaction. FIG. 17C illustrates the actual NA sequences of the target NA and the anchor and sequencing probe. FIG. 17D illustrates anchor probe staining of RCPs immobilized on the glass surface. The top image in the left column of FIG. 17E is a zoom in area from the anchor stain in FIG. 17D. The bottom image in the left column of FIG. 17E is a base call plotted on top of the anchor stain. The images in the right columns of FIG. 17E are summed images of 20 individual time points with arbitrary intermediate interval for all 4 fluorescent channels, corresponding to the base-specific staining: G, C, T and A. Base calling was based on the channel with the highest S/N ratio, as already described above.

Example 3: Profiling of Individual RNA Molecules Inside Preserved Human Cells by Time Resolved Sequencing by Hybridization (tr-SBH)

Preparation of Cell System for Sequencing

A-549 cells were cultured in Dulbecco's modified Eagle's medium (DMEM) (Gibco) without phenol red and L-glutamine, supplemented with 10% fetal bovine serum (FBS) (Sigma), 2 mM L-glutamine (Sigma) and 1× protein tyrosine phosphatase (PEST) (Sigma). The cells were incubated at 37° C., 5% $CO_2$. To seed cells on cover slips (#1.5, thickness: 1.7 mm), confluent cells were treated with 0.25% (w/v) trypsin-EDTA (Sigma) and resuspended in culturing medium. Resuspended cells were then seeded on cover slips (No 1.5, VWR) placed in a 150 mm×25 mm Petri dish (Corning), and culturing medium was added to a final volume of 25 ml. Three millilitres of resuspended cells were used to seed five cover slips. Cells were incubated at 37° C., 5% $CO_2$ overnight. Fixation was performed in 3.7% (v/v) paraformaldehyde (Sigma) in dimethylpyrocarbonate (DEPC) treated PBS for 15 min at room temperature (RT) after removal of the culturing medium and two washes in PBS. After fixation, the cover slips were washed twice in DEPC-treated PBS and dehydrated in an ethanol series of 70% and 100% for 5 min each. The cover slips were stored at −80° C. until use. A respective flow cell was then attached to the fixed cells on the cover slips and all of the following reactions were performed in the flow cell.

NAA Preparation by RCA for Sequencing In Situ

A barcoded circular probe (padlock probe) with barcode sequence ATCG was hybridized and ligated. A ligation mixture containing 1× SplintR® (ligase buffer), 100 nM of padlock probe, 0.5 U/μl SplintR® (ligase) (NEB) and 0.8 U/μl RNasIn® (ribonuclease inhibitor, DNAGdansk) was added to each reaction chamber. The incubation was carried out at 37° C. for 30 min. The cover slip was washed with 1×PBS-T twice. RCA was primed by the target strand. RCA mixture containing 1 U/μl phi29 polymerase (Olink), 1× phi29 polymerase buffer, 0.25 mM dNTPs, 0.2 μg/μl BSA and 5% glycerol in $H_2O$ was added to the reaction chamber and incubated overnight at RT. After the incubation, the cover slip was washed twice in PBS-T.

Tr-SBH In Situ Inside Preserved Cells

A hybridization mixture containing 20 nM of each oligonucleotide probe (see probe sequences below), 1× T4 ligase buffer (DNAGdansk), 1 mM ATP (Fermentas) at RT was applied to the samples through the flow cell. The hybridization reaction of the competing oligonucleotide probes was monitored by imaging over time, as described below. The third base of the ATCG barcode was interrogated, see FIG. 14.

Imaging and Image Processing of tr-SBH Reaction

A widefield fluorescence microscope described in Example 1 was used to monitor time-resolved sequencing reactions. Continuous image series were recorded for each channel (100 ms exposures, approximately 10 frames) at multiple time points (interval: approximately 1 min, 9 time points), stored as raw data and exported as TIFF files for image processing.

A fluorescently-labeled anchor primer was first hybridized to the NAA to assist focusing before base interrogation by the SBH oligonucleotide probes, see FIG. 10.

Recorded raw data of individual frames of anchor probe and oligonucleotide probes were exported as TIFF files. Average intensity projections were calculated from the anchor primer image series after washing. In CellProfiler [1], the projection image was high-pass (top-hat) filtered to emphasize RCP-sized details and to suppress lower frequencies corresponding to larger details such as nuclei and cell body. The resulting size-filtered images were segmented into RCP areas 1 and surrounding local background 2, see FIG. 7, based on an empirically determined manual intensity threshold. Intensity values $I_1$ and $I_2$ were extracted from both compartments 1, 2 in FIG. 7. The ratios between RCP intensity ($I_1$) and intensity of local background ($I_2$) were calculated for individual amplicons at multiple time points. A minimum of 5 frames was integrated per time point to discern signals from background.

Figure 14:
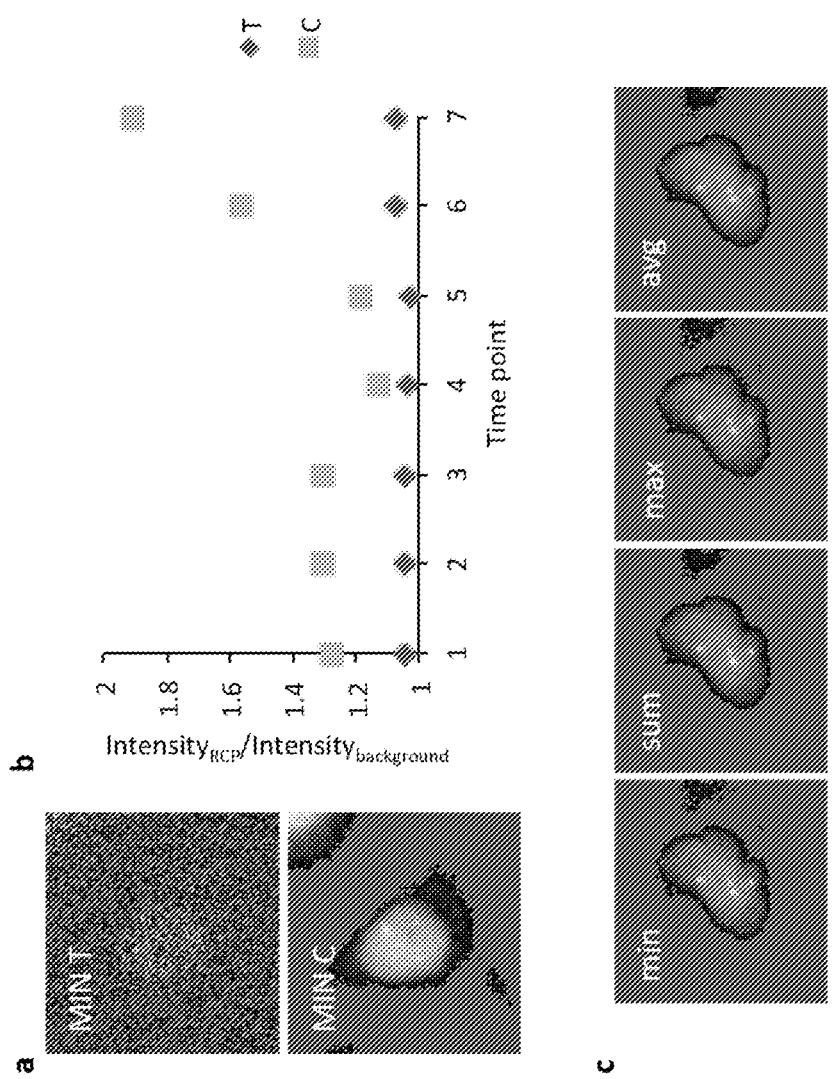
FIG. 14 illustrates the results of an in situ SBH experiment inside preserved cells involving sequencing by hybridization of the $3^{rd}$ base (C) of a barcode sequence coding for Actin beta inside human A549 cells. a) Minimum intensity projections allow for discrimination of signal from background. b) Signal-to-noise ratio (minimum intensity in RCP defining area/minimum intensity in local background) of a single RCP at 7 time points. X axis: arbitrary time points. The correct base (C) can be called at any time point. c) In addition to integrating minimum intensity values, signals can also be discriminated by calculating average and maximum intensity projections as well as by summing up frames from different time points.

FIG. 14 illustrates the results of the tr-SBH experiment involving sequencing by hybridization of the $3^{rd}$ base (C) of a barcode sequence coding for Actin beta inside human A549 cells. FIG. 14A illustrates that minimum intensity projections allow for discrimination of signal from background. FIG. 14B illustrates signal to noise ratio (minimum intensity in RCP defining area/minimum intensity in local background) of a single RCP at 7 time points. X axis: arbitrary time points. The correct base (C) can be called at any time point. In addition to integrating minimum intensity values, signals can also be discriminated by calculating average and maximum intensity projections as well as by summing up frames of different time points as shown in FIG. 14C.

Example 4: Profiling of Individual RNA Molecules Inside a 10 μm Tissue Section of Preserved Mouse Brain by Time Resolved Sequencing by Hybridization (tr-SBH)

Preparation of Tissue System for Sequencing

Microscope-slide mounted, fresh-frozen tissue sections of mouse brain were fixed in 3.7% (v/v) paraformaldehyde (Sigma) in dimethylpyrocarbonate (DEPC) treated PBS for 5 min at room temperature (RT). After fixation, the specimens were washed twice in DEPC-treated PBS and dehydrated in an ethanol series of 70% and 100% for 5 min each. The specimens were stored at −80° C. until use. A respective flow cell was then attached to the fixed cells on the cover slips and all of the following reactions were performed in the flow cell.

NAA Preparation by RCA for Sequencing In Situ

A hydrophobic barrier was drawn around the tissue section using a PAP pen (Sigma Aldrich). All reaction steps were carried out inside a humid chamber that was constructed from an empty micropipette tip box. To provide a humid environment, water was added to the tip box. RNA was in situ reverse transcribed to cDNA. A ligation mixture containing 1× reverse transcription buffer, 5 μM of random decamer primer, 0.2 mM dNTP, 0.2 μg/μl BSA, 20 U/μl TranscriptMe (DNA Gdansk) and 1 U/μl RNasIn® (ribonuclease inhibitor, DNA Gdansk) was added to the slide. The incubation was carried out overnight at 37° C. The specimen was washed in PBS-T twice. A pool of barcoded circular probes (padlock probes) was hybridized and ligated in situ to cDNA. A reaction mixture containing 1× ligation buffer, 0.05 M KCl, 20% formamide, 100 nM probes (padlock probes), 0.2 μg/μl BSA, 0.5 U/μl Ampligase® (DNA ligase) (epicenter) and 0.4 U/μl RNase H (DNA Gdansk) was added to the slide. The specimen was washed in PBS-T twice. RCA was primed by the target strand. RCA mixture containing 1 U/μl phi29 polymerase (Olink), 1× phi29 polymerase buffer, 0.25 mM dNTPs, 0.2 μg/μl BSA and 5% glycerol in $H_2O$ was added to the specimen and incubated overnight at RT. After the incubation, the specimen was washed in PBS-T twice.

Tr-SBH In Situ Inside Preserved Mouse Brain

A fluorescently-labelled anchor primer was first hybridized to the RCPs to assist focusing before base interrogation by the SBH oligonucleotide probes (see FIG. 9).

A hybridization mixture containing 20 nM of each oligonucleotide probe (see probe sequences below), 1× T4 ligase buffer (DNAGdansk), 1 mM ATP (Fermentas) at RT was applied to the samples while being mounted in the microscope stage. The hybridization reaction of the competing oligonucleotide probes was monitored by imaging over time, as described below. The second base of each barcode was interrogated, see FIG. 15.

Imaging and Image Processing of tr-SBH Reaction

A widefield fluorescence microscope essentially as described in Example 1 was used to monitor time-resolved sequencing reactions employing a water-dipping Zeiss W Plan-Apochromat 40×/1.0 DIC objective instead of the 20× objective used in Example 1. For imaging, the objective was directly submerged into hybridization mixture. 10 subsequent Z-stack image series were recorded for each channel (100 ms exposure per image, 10 focal planes, 1 μm interval per image Z-stack), and stored as raw data. Image Z-stacks were projected as orthogonal maximum intensity projections (MIPs) and exported as TIFF files for image processing.

In CellProfiler [1], the maximum, average and sum of intensity values were calculated per pixel for every channel. The range of intensity values was scaled to utilize the full bit depth.

Figure 15:
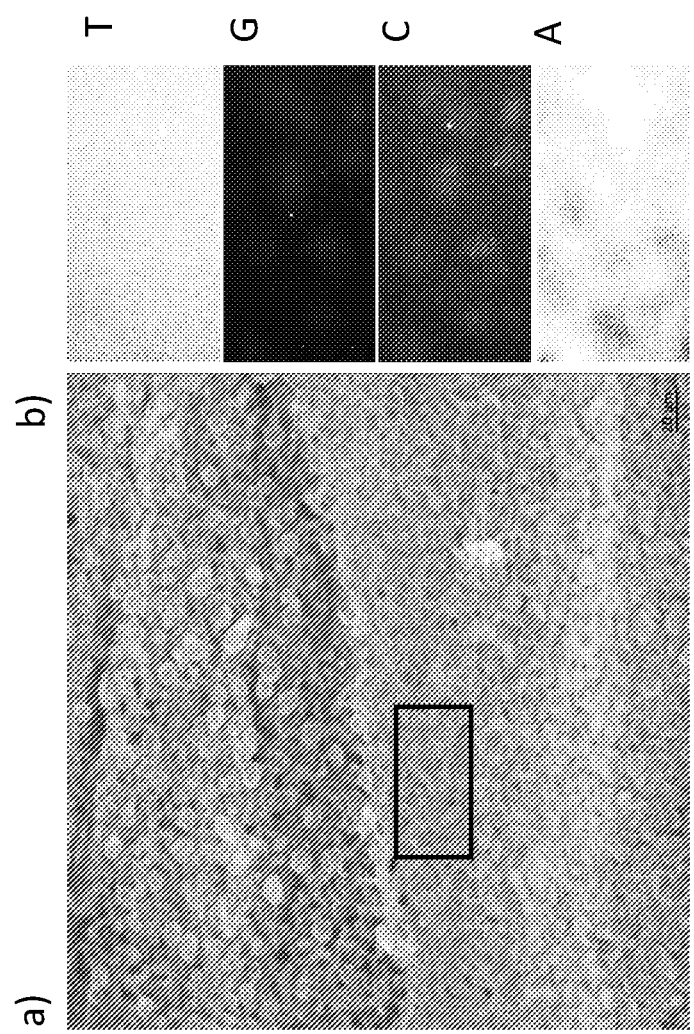
FIG. 15 illustrates the results of an in situ SBH experiment to sequence the second base of 4-base barcodes in RCPs generated in situ in a section of preserved mouse brain. a) Depicts a nuclei-stained field of view of the tissue section. The rectangular box outlines the region depicted in b) Maximum-intensity projections of 10 frames (acquired in 1 min intervals) are shown for SBH libraries interrogating Thymine (T), Guanine (G), Cytosine (C) and Adenosine (A). Signals are detected as white speckles in G and C.

FIG. 15 illustrates the results of an in situ SBH experiment to sequence the second base of 4-base barcodes in RCPs generated in situ in a section of preserved mouse. FIG. 15A depicts a nuclei-stained field of view of the tissue section. The rectangular box outlines the region depicted in FIG. 15B. Maximum-intensity projections of 10 frames (acquired in 1 min intervals) are shown for SBH libraries interrogating Thymine (T), Guanine (G), Cytosine (C) and Adenosine (A). Signals are detected as white speckles in G and C.

Example 5: Barcode Sequencing of Single Molecule Fluorescence In Situ Hybridization (smFISH) NAAs for Multiplexed Analysis of RNA Molecules Inside Individual Preserved Cells and Tissues by Time Resolved Sequencing by Hybridization (tr-SBH)

Preparation of Cells

MCF7 cells were cultured, and seeded on cover slips, as described for A549 cells above. After fixation the cover slips were stored at +4° C. in 70% ethanol until use.

NAA Preparation by Single Molecule Fluorescence In Situ Hybridization (smFISH)

48 smFISH probes, with varying target specific sequences against different regions on the her2 gene, and general overhang sequence carrying a gene-specific barcode (illustrated in FIG. 10) were hybridized in hybridization buffer containing 2×SSC, 10% dextran sulfate, 25% formamide, 1 mg/mL E. coli tRNA and 0.02% BSA for 16 h at 30° C. The cells were washed in 2×SSC, 25% formamide containing wash buffer for 1 h at 30° C. twice.

Tr-SBH on smFISH Inside Preserved Cells

A general anchor probe (100 nM final concentration) was hybridized to the smFISH overhang in hybridization buffer for 1 h at 30° C. The cells were washed in wash buffer for 1 h at 30° C. Cell nuclei were stained with DAPI as described above and rinsed in 2×SSC. The cells were then immersed in sequencing mixture, containing 0.5 nM each smFISH-sequencing oligonucleotide in 2×SSC, 10 mM Tris-HCl pH 7.5, 0.4% glucose, 10 mM Trolox, 37 ng/μL glucose oxidase and catalase by mounting the cover slips with the cells on a standard microscope glass slide and sealing the cover slip to avoid evaporation. The reaction was first incubated for 15 min at room temperature to ensure sufficient diffusion to the target NAs inside the cells. Then the slides were mounted in a Nikon microscope with LED illumination system and imaged with oil immersion 100× objective. First cells were focused on the approximate middle layer of the nuclei staining. Then 25 images were acquired in all channels with 200 ms exposure time for each at multiple time points with approximate interval of 2 seconds. Images were stored and exported as TIFF files for image processing.

Image Processing of smFISH tr-SBH Reaction

Recorded raw data of individual frames of the smFISH sequencing oligonucleotide probes were exported as TIFF files. Average intensity projections were calculated for all 25 frames.

FIG. 18 illustrates the results of the tr-SBH smFISH experiment of the gene-specific barcode sequence in the general overhang sequence for the her2 gene in MCF7 cells. FIG. 18A shows the nuclei staining and the region of interest, zoomed into in the images in FIG. 18B. Top panel images of FIG. 18B are individual frames (1 image) of all fluorescent channels G, T and A. Only one or two smFISH signals may be slightly visible in the A-Cy® 5 (dye) channel with 1 frame. Bottom panel images of FIG. 18B illustrate average intensity projections of 25 frames for each fluorescent channel G, T and A. Several smFISH signals are distinguishable above the background after image integration only in the base A-specific Cy® 5 (dye) channel (see white arrows).

```
Oligonucleotide probes
Barcode sequencing probes
Barcode sequencing probes base 1
```

5'-Phos-ANNNCTATC-3'-Cy®5 (dye) (SEQ ID NO: 25)
5'-Phos-CNNNCTATC-3'-TexasRed® (dye) (SEQ ID NO: 26)
5'-Phos-TNNNCTATC-3'-AF488 (Alexa Flour® 488) (dye) (SEQ ID NO: 27)
5'-Phos-GNNNCTATC-3'-Cy®3 (dye) (SEQ ID NO: 28)

Barcode sequencing probes base 2

5'-Phos-NANNCTATC-3'-Cy®5 (dye) (SEQ ID NO: 11)
5'-Phos-NCNNCTATC-3'-TexasRed® (dye) (SEQ ID NO: 13)
5'-Phos-NTNNCTATC-3'-AF488 (Alexa Flour® 488) (dye) (SEQ ID NO: 12)
5'-Phos-NGNNCTATC-3'-Cy®3 (dye) (SEQ ID NO: 10)

Barcode sequencing probes base 3

5'-Phos-NNANCTATC-3'Cy®5 (dye) (SEQ ID NO: 29)
5'-Phos-NNCNCTATC-3'-TexasRed® (dye) (SEQ ID NO: 30)
5'-Phos-NNTNCTATC-3'AF488 (Alexa Flour® 488) (dye) (SEQ ID NO: 31)
5'-Phos-NNGNCTATC-3'-Cy®3 (dye) (SEQ ID NO: 32)

NA molecule sequencing probes 1$^{st}$ base

5'-Phos-ANNNNNNNN-3'-Cy®5 (dye) (SEQ ID NO: 21)
5'-Phos-CNNNNNNNN-3'-TexasRed® (dye) (SEQ ID NO: 19)
5'-Phos-TNNNNNNNN-3'-AF488 (Alexa Flour® 488) (dye) (SEQ ID NO: 20)
5'-Phos-GNNNNNNNN-3'-Cy®3 (dye) (SEQ ID NO: 22)

smFISH probe overhang sequence

5'-TTTTCTAGCTTTAGGGTTAGCGAAG-3' (SEQ ID NO: 6)

smFISH barcode sequencing probes 1$^{st}$ base

5'-TAAANNNAGA-3'-Cy®5 (dye) (SEQ ID NO: 25)
5'-TAACNNNAGA-3' (SEQ ID NO: 34)
5'-TAATNNNAGA-3'-AF488 (Alexa Flour® 488) (dye) (SEQ ID NO: 35)
5'-TAAGNNNAGA-3'-Cy®3 (dye) (SEQ ID NO: 36)

Anchor probes

5'-Cy3-UGCGUCUAUUUAGUGGAGCC-3' (SEQ ID NO: 1)
5'-AlexaFluor750-UGCGUCUAUUUAGUGGAGCC-3' (SEQ ID NO: 1)
smFISH anchor probe: 5'-CTTCGCTAACCC-3' (SEQ ID NO: 7)

Padlock probe used in SBL experiment

5'-Phos-
AGCCTCGCCTTTGCCTCCTCTATGATTACTGACTGCGTCTATTTAGTGGA
GCCGCATCTATCTTCTTTCGCCCCGCGAGCACAG-3' (SEQ ID NO: 2)

Padlock probe used in SBH experiment

5'-Phos-
CCTGTGGCTGGTCTGATTCCTTTGACTCACATTTCTTTTGCGTCTATTTA
GTGGAGCCATCGCTATCATACTTTATTGGACATCT-3' (SEQ ID NO: 3)
5'-Phos-
GTTTTCTTTCAGACAGAATCCGTGCTTGTGGTAGCAAATATGCGTCTATT
TAGTGGAGCCACTGCTATCTTCTTTTTAGTTGGTATTATTGTCATTTT-3' (SEQ ID NO: 8)
5'-Phos-
CCTGGATTCTTCTTGGCGTGCTTGTGGTAGCAAATATGCGTCTATTTAGT
GGAGCCTGGTCTATCTTCTTTTGTCATTGCTGAGGTAG-3' (SEQ ID NO: 9)

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

[1] Kamentsky et al., Improved structure, function, and compatibility for CellProfiler modular high-throughput image analysis software, *Bioinformatics Advance Access*, Feb. 23, 2011
[2] US patent application no. 2012/0129165
[3] Ke et al., In situ sequencing for RNA analysis in preserved tissue and cells, *Nature Methods,* 2013, 10(9): 857-862
[4] Shendure et al., Accurate multiplex polony sequencing of an evolved bacterial genome, *Science,* 2005, 309(5741): 1728-1732

The invention claimed is:

1. A method comprising:
a) performing measurement of at least two time points for:
i) a hybridization reaction comprising hybridization of one or more oligonucleotide probes to a target nucleic acid sequence; or
ii) a ligation reaction comprising ligation of one or more oligonucleotide probes to an anchor probe complementary to a segment of a nucleic acid molecule comprising a target nucleic acid sequence,
wherein the hybridization reaction or the ligation reaction is at at least one spatially defined site,
wherein the one or more oligonucleotide probes either lack a label or have a different label,
wherein the measurement comprises measuring a label or absence thereof at the at least one spatially defined site,
wherein one or more of the at least two time points are prior to the end point of the hybridization reaction or the ligation reaction, and
wherein at least two data sets are generated from the measurement, one for each of the at least two time points;
b) detecting the label or absence thereof of the one or more oligonucleotide probes at the at least one spatially defined site by co-processing the at least two data sets; and
c) determining a sequence of the target nucleic acid sequence at the at least one spatially defined site based on the detecting in step b), wherein determining the sequence comprises sequencing by the hybridization or ligation reaction.

2. The method according to claim 1, wherein the target nucleic acid sequence is contacted with at least two oligonucleotide probes, wherein:
i) each of the at least two oligonucleotide probes has a different nucleic acid sequence; and
iia) the at least two oligonucleotide probes have different labels, or
iib) an oligonucleotide probe of the at least two oligonucleotide probes lacks a label and the rest of the at least two oligonucleotide probes have different labels.

3. The method according to claim 2, wherein the target nucleic acid sequence is contacted with four oligonucleotide probes, wherein each of the four oligonucleotide probes has a different nucleotide at a specific base position of the four oligonucleotide probes.

4. The method according to claim 1, wherein the at least two time points are separated from each other by at least 20 ns during the hybridization reaction the ligation reaction.

5. The method according to claim 1, wherein the measurement comprises light measurements.

6. The method according to claim 5, wherein the light measurements comprise measuring fluorescence, and the at least two data sets comprise fluorescence data sets.

7. The method according to claim 6, wherein the light measurements comprise measuring fluorescence intensity in one or more fluorescence channels each for measuring a fluorescent label of the one or more oligonucleotide probes.

8. The method according to claim 1, wherein co-processing the at least two data sets comprises:
for each of the one or more oligonucleotide probes having a label, generating a combined data set of signal intensity projection of the label from the at least two data sets; and
identifying the label or absence thereof at the at least one spatially defined site based on the combined data sets.

9. The method according to claim 1, wherein co-processing the at least two data sets comprises:
for each of the one or more oligonucleotide probes having a label, generating a combined data set by summing intensity values of the label from the at least two data sets; and
identifying the label or absence thereof at the at least one spatially defined site based on the combined data sets.

10. The method according to claim 1, wherein co-processing the at least two data sets comprises:
for each of the one or more oligonucleotide probes having a label, generating a combined data set by averaging intensity values of the label from the at least two data sets; and
identifying the label or absence thereof at the at least one spatially defined site based on the combined data sets.

11. The method according to claim 7, wherein:
the light measurements comprise light measurements at the at least one spatially defined site and outside of the at least one spatially defined site; and the detecting in step b) comprises
identifying the fluorescent label or absence thereof at the at least one spatially defined site based on a quotient between intensity values at the at least one spatially defined site and outside of the at the at least one spatially defined site.

12. The method according to claim 1, wherein:
the measurement comprises light measurements at the at least one spatially defined site and outside of the at least one spatially defined site; and
co-processing the at least two data sets comprises:
calculating, for each data set of the at least two data sets, a quotient between intensity values at the at least one spatially defined site and outside of the at least one spatially defined site; and
identifying the label or absence thereof at the at least one spatially defined site based on the quotients.

13. The method according to claim 1, wherein the target nucleic acid sequence is contacted with the one or more oligonucleotide probes in the presence of a ligating enzyme and the anchor probe, wherein the segment is adjacent to the target nucleic acid sequence.

14. The method according to claim 1, further comprising immobilizing i) a nucleic acid molecule comprising the target nucleic acid sequence or ii) a nucleic acid molecule that is hybridized to another nucleic acid molecule comprising the target nucleic acid sequence onto a solid support to form the target nucleic acid sequence at the at least one spatially defined site.

15. The method according to claim 1, further comprising immobilizing a nucleic acid molecule comprising the target nucleic acid sequence in a gel matrix to form the target nucleic acid sequence at the at least one spatially defined site.

16. The method according to claim 1, further comprising:
removing the one or more oligonucleotide probes;
repeating the performing measurement step and the detecting step with another one or more oligonucleotide probes, optionally without a washing step prior to contacting the target nucleic acid sequence with the another one or more oligonucleotide probes; and
determining another sequence of the target nucleic acid sequence at the at least one spatially defined site based on the detecting step with the another one or more oligonucleotide probes.

17. The method according to claim 16, wherein the another one or more oligonucleotide probes have a higher affinity to the target nucleic acid sequence as compared to the one or more oligonucleotide probes.

18. The method of claim 1, wherein the performing measurement step, the detecting step, and the determining step are repeated to perform sequencing by ligation (SBL) or sequencing by ligation (SBH) of a rolling circle amplification product.

19. The method of claim 1, wherein the method is performed in situ in a cell or tissue sample.

20. The method of claim 1, wherein in b) the one or more oligonucleotide probes are detected at the at least one spatially defined site by co-processing the at least two data sets.

* * * * *

UNITED STATES PATENT AND TRADEMARK OFFICE
CERTIFICATE OF CORRECTION

PATENT NO. : 11,352,667 B2
APPLICATION NO. : 16/312994
DATED : June 7, 2022
INVENTOR(S) : Thomas Hauling et al.

It is certified that error appears in the above-identified patent and that said Letters Patent is hereby corrected as shown below:

In the Claims

At Column 50, Claim number 4, Line number 29, please replace "the hybridization reaction the ligation reaction" with --the hybridization reaction or the ligation reaction--

At Column 52, Claim number 18, Line number 22, please replace "sequencing by ligation (SBH)" with --sequencing by hybridization (SBH)--

Signed and Sealed this
Eighteenth Day of April, 2023

Katherine Kelly Vidal
*Director of the United States Patent and Trademark Office*

```
SEQUENCE LISTING

<160> NUMBER OF SEQ ID NOS: 36

<210> SEQ ID NO 1
<211> LENGTH: 20
<212> TYPE: RNA
<213> ORGANISM: Artificial Sequence
<220> FEATURE:
<223> OTHER INFORMATION: Anchor primer for SBL/SBH

<400> SEQUENCE: 1
ugcgucuauu uaguggagcc                                                   20

<210> SEQ ID NO 2
<211> LENGTH: 84
<212> TYPE: DNA
<213> ORGANISM: Artificial Sequence
<220> FEATURE:
<223> OTHER INFORMATION: Padlock probe for SBL
<220> FEATURE:
<221> NAME/KEY: misc_feature
<222> LOCATION: (54)..(57)
<223> OTHER INFORMATION: Barcode sequence

<400> SEQUENCE: 2
agcctcgcct ttgcctcctc tatgattact gactgcgtct atttagtgga gccgcatcta      60
tcttctttcg ccccgcgagc acag                                             84

<210> SEQ ID NO 3
<211> LENGTH: 85
<212> TYPE: DNA
<213> ORGANISM: Artificial Sequence
<220> FEATURE:
<223> OTHER INFORMATION: Padlock probe for SBH
<220> FEATURE:
<221> NAME/KEY: misc_feature
<222> LOCATION: (59)..(62)
<223> OTHER INFORMATION: Barcode sequence

<400> SEQUENCE: 3
cctgtggctg gtctgattcc tttgactcac atttcttttg cgtctattta gtggagccat      60
cgctatcata ctttattgga catct                                            85

<210> SEQ ID NO 4
<211> LENGTH: 29
<212> TYPE: DNA
<213> ORGANISM: Artificial Sequence
<220> FEATURE:
<223> OTHER INFORMATION: RCA product with CGTA barcode complementary
      sequence

<400> SEQUENCE: 4
acgcagataa atcacctcgg cgtagatag                                        29
```

```
<210> SEQ ID NO 5
<211> LENGTH: 29
<212> TYPE: DNA
<213> ORGANISM: Artificial Sequence
<220> FEATURE:
<223> OTHER INFORMATION: RAC product with TAGC barcode complementary
      sequence

<400> SEQUENCE: 5
acgcagataa atcacctcgg tagcgatag                                    29

<210> SEQ ID NO 6
<211> LENGTH: 25
<212> TYPE: DNA
<213> ORGANISM: Artificial Sequence
<220> FEATURE:
<223> OTHER INFORMATION: smFISH probe overhang sequence

<400> SEQUENCE: 6
ttttctagct ttagggttag cgaag                                        25

<210> SEQ ID NO 7
<211> LENGTH: 12
<212> TYPE: DNA
<213> ORGANISM: Artificial Sequence
<220> FEATURE:
<223> OTHER INFORMATION: smFISH anchor probe

<400> SEQUENCE: 7
cttcgctaac cc                                                      12

<210> SEQ ID NO 8
<211> LENGTH: 98
<212> TYPE: DNA
<213> ORGANISM: Artificial Sequence
<220> FEATURE:
<223> OTHER INFORMATION: Padlock probe for SBH
<220> FEATURE:
<221> NAME/KEY: misc_feature
<222> LOCATION: (61)..(64)
<223> OTHER INFORMATION: Barcode sequence

<400> SEQUENCE: 8
gttttctttc agacagaatc cgtgcttgtg gtagcaaata tgcgtctatt tagtggagcc  60
actgctatct tcttttagt tggtattatt gtcatttt                           98

<210> SEQ ID NO 9
<211> LENGTH: 88
<212> TYPE: DNA
<213> ORGANISM: Artificial Sequence
<220> FEATURE:
<223> OTHER INFORMATION: Padlock probe for SBH
<220> FEATURE:
<221> NAME/KEY: misc_feature
<222> LOCATION: (57)..(60)
<223> OTHER INFORMATION: Barcode sequence

<400> SEQUENCE: 9
cctggattct tcttggcgtg cttgtggtag caaatatgcg tctatttagt ggagcctggt  60
ctatcttctt ttgtcattgc tgaggtag                                     88

<210> SEQ ID NO 10
<211> LENGTH: 9
<212> TYPE: DNA
<213> ORGANISM: Artificial Sequence
```

```
<220> FEATURE:
<223> OTHER INFORMATION: Synthetic construct
<220> FEATURE:
<221> NAME/KEY: misc_feature
<222> LOCATION: 1, 3, 4
<223> OTHER INFORMATION: n = A,T,C or G

<400> SEQUENCE: 10 ngnnctatc                                                                    9

<210> SEQ ID NO 11
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1, 3, 4
<223> OTHER INFORMATION: n = A,T,C or G

<400> SEQUENCE: 11 nannctatc                                                                    9

<210> SEQ ID NO 12
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1, 3, 4
<223> OTHER INFORMATION: n = A,T,C or G

<400> SEQUENCE: 12 ntnnctatc                                                                    9

<210> SEQ ID NO 13
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1, 3, 4
<223> OTHER INFORMATION: n = A,T,C or G

<400> SEQUENCE: 13 ncnnctatc                                                                    9

<210> SEQ ID NO 14
<211> LENGTH: 9
<212> TYPE: DNA
<213> ORGANISM: Artificial Sequence
<220> FEATURE:
<223> OTHER INFORMATION: Synthetic construct

<400> SEQUENCE: 14 aaaagctaa                                                                    9

<210> SEQ ID NO 15
<211> LENGTH: 10
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<222> LOCATION: 4, 6, 7
<223> OTHER INFORMATION: n = A,T,C or G

<400> SEQUENCE: 15 aaancnnaaa                                                              10

<210> SEQ ID NO 16
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4, 6, 7
<223> OTHER INFORMATION: n = A,T,C or G

<400> SEQUENCE: 16 aaangnnaaa                                                              10

<210> SEQ ID NO 17
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4, 6, 7
<223> OTHER INFORMATION: n = A,T,C or G

<400> SEQUENCE: 17 aaanannaaa                                                              10

<210> SEQ ID NO 18
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4, 6, 7
<223> OTHER INFORMATION: n = A,T,C or G

<400> SEQUENCE: 18 aaantnnaaa                                                              10

<210> SEQ ID NO 19
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 2, 3, 4, 5, 6, 7, 8, 9
<223> OTHER INFORMATION: n = A,T,C or G

<400> SEQUENCE: 19 cnnnnnnnn                                                                9

<210> SEQ ID NO 20
<211> LENGTH: 9
<212> TYPE: DNA
<213> ORGANISM: Artificial Sequence
<220> FEATURE:
<223> OTHER INFORMATION: Synthetic construct
```

```
<220> FEATURE:
<221> NAME/KEY: misc_feature
<222> LOCATION: 2, 3, 4, 5, 6, 7, 8, 9
<223> OTHER INFORMATION: n = A,T,C or G

<400> SEQUENCE: 20 tnnnnnnnn                                                            9

<210> SEQ ID NO 21
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 2, 3, 4, 5, 6, 7, 8, 9
<223> OTHER INFORMATION: n = A,T,C or G

<400> SEQUENCE: 21 annnnnnnn                                                            9

<210> SEQ ID NO 22
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 2, 3, 4, 5, 6, 7, 8, 9
<223> OTHER INFORMATION: n = A,T,C or G

<400> SEQUENCE: 22 gnnnnnnnn                                                            9

<210> SEQ ID NO 23
<211> LENGTH: 29
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 22, 23, 24, 25, 26, 27, 28, 29
<223> OTHER INFORMATION: n = A,T,C or G

<400> SEQUENCE: 23
tgcgtctatt tagtggagcc gnnnnnnnn                                     29

<210> SEQ ID NO 24
<211> LENGTH: 44
<212> TYPE: DNA
<213> ORGANISM: Artificial Sequence
<220> FEATURE:
<223> OTHER INFORMATION: Synthetic construct

<400> SEQUENCE: 24
aagaagatag atgcggctcc actaaataga cgcagtcagt aatc                    44

<210> SEQ ID NO 25
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 2, 3, 4
```

```
<223> OTHER INFORMATION: n = A,T,C or G

<400> SEQUENCE: 25 annnctatc                                                                 9

<210> SEQ ID NO 26
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 2, 3, 4
<223> OTHER INFORMATION: n = A,T,C or G

<400> SEQUENCE: 26 cnnnctatc                                                                 9

<210> SEQ ID NO 27
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 2, 3, 4
<223> OTHER INFORMATION: n = A,T,C or G

<400> SEQUENCE: 27 tnnnctatc                                                                 9

<210> SEQ ID NO 28
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 2, 3, 4
<223> OTHER INFORMATION: n = A,T,C or G

<400> SEQUENCE: 28 gnnnctatc                                                                 9

<210> SEQ ID NO 29
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1, 2, 4
<223> OTHER INFORMATION: n = A,T,C or G

<400> SEQUENCE: 29 nnanctatc                                                                 9

<210> SEQ ID NO 30
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
```

```
<222> LOCATION: 1, 2, 4
<223> OTHER INFORMATION: n = A,T,C or G

<400> SEQUENCE: 30 nncnctatc                                                                9

<210> SEQ ID NO 31
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1, 2, 4
<223> OTHER INFORMATION: n = A,T,C or G

<400> SEQUENCE: 31 nntnctatc                                                                9

<210> SEQ ID NO 32
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1, 2, 4
<223> OTHER INFORMATION: n = A,T,C or G

<400> SEQUENCE: 32 nngnctatc                                                                9

<210> SEQ ID NO 33
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 5, 6, 7
<223> OTHER INFORMATION: n = A,T,C or G

<400> SEQUENCE: 33 taaannnaga                                                              10

<210> SEQ ID NO 34
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 5, 6, 7
<223> OTHER INFORMATION: n = A,T,C or G

<400> SEQUENCE: 34 taacnnnaga                                                              10

<210> SEQ ID NO 35
<211> LENGTH: 10
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<222> LOCATION: 5, 6, 7
<223> OTHER INFORMATION: n = A,T,C or G

<400> SEQUENCE: 35 taatnnnaga                                                              10

<210> SEQ ID NO 36
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 5, 6, 7
<223> OTHER INFORMATION: n = A,T,C or G

<400> SEQUENCE: 36 taagnnnaga                                                              10
```